US010899863B2

(12) United States Patent
Jakubowski et al.

(10) Patent No.: US 10,899,863 B2
(45) Date of Patent: *Jan. 26, 2021

(54) OIL SOLUBLE RHEOLOGY MODIFYING STAR MACROMOLECULES

(71) Applicant: Pilot Polymer Technologies, Inc., Pittsburgh, PA (US)

(72) Inventors: Wojciech Jakubowski, Sugar Land, TX (US); Patrick McCarthy, Pittsburgh, PA (US); Nicolay Tsarevsky, Dallas, TX (US); James Spanswick, Pittsburgh, PA (US)

(73) Assignee: Pilot Polymer Technologies, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,763

(22) Filed: Jun. 22, 2016

(65) Prior Publication Data
US 2017/0051094 A1  Feb. 23, 2017

Related U.S. Application Data

(63) Continuation of application No. 14/036,993, filed on Sep. 25, 2013, now Pat. No. 9,399,694, which is a (Continued)

(51) Int. Cl.
*C08F 293/00* (2006.01)
*A61K 8/81* (2006.01)
(Continued)

(52) U.S. Cl.
CPC ........ *C08F 293/005* (2013.01); *A61K 8/8152* (2013.01); *A61K 8/90* (2013.01); (Continued)

(58) Field of Classification Search
CPC .. C08F 287/00; C08F 285/00; C08J 2300/206
See application file for complete search history.

(56) References Cited

U.S. PATENT DOCUMENTS 4,386,135 A  5/1983  Campbell et al.
4,409,120 A  10/1983  Martin
(Continued)

FOREIGN PATENT DOCUMENTS

DE  102005041528 A1  3/2007
EP       422805 A     4/1991
(Continued)

OTHER PUBLICATIONS

Hadjichristidis Prog. Polym. Sci. 2006, 31, 1068-1132 (Year: 2006).*
(Continued)

*Primary Examiner* — Mark S Kaucher
(74) *Attorney, Agent, or Firm* — Ulmer & Berne, LLP

(57) ABSTRACT

Oil soluble rheology modifying star macromolecules having a core and five or more polymeric arms, and compositions comprising the same. The polymeric arms on a star are covalently attached to the core of the star; each polymeric arm comprises one or more (co)polymer segments; and each polymeric arm comprises a monomeric unit of a methyl methacrylate. The oil soluble rheology modifying star macromolecules and compositions comprising the same for use in oil based systems.

13 Claims, 15 Drawing Sheets

Star macromolecule with segmented arms     Mikto-arm star macromolecule with homopolymer arms     Mikto-arm star macromolecule with arms of mixed composition

Related U.S. Application Data continuation of application No. 12/799,411, filed on Apr. 23, 2010, now Pat. No. 8,569,421.

(60) Provisional application No. 61/214,397, filed on Apr. 23, 2009.

(51) Int. Cl.
    *A61Q 19/00*     (2006.01)
    *A61K 8/90*     (2006.01)
    *C08G 83/00*     (2006.01)

(52) U.S. Cl.
    CPC ............ *A61Q 19/00* (2013.01); *C08F 293/00* (2013.01); *C08G 83/003* (2013.01); *A61K 2800/10* (2013.01); *A61K 2800/48* (2013.01); *A61K 2800/544* (2013.01); *C08F 2438/01* (2013.01); *C08F 2438/03* (2013.01); *C08J 2300/206* (2013.01)

(56) References Cited

U.S. PATENT DOCUMENTS

| | | | |
|---|---|---|---|
| 4,474,924 A * | 10/1984 | Powers | C08F 6/24 524/465 |
| 4,847,328 A | 7/1989 | Hutchins et al. | |
| 5,240,963 A | 8/1993 | Domb et al. | |
| 5,362,813 A | 11/1994 | Antonelli et al. | |
| 5,486,563 A | 1/1996 | Sutherland | |
| 5,545,342 A | 8/1996 | Beagle et al. | |
| 5,545,504 A | 8/1996 | Keoshkerian et al. | |
| 5,594,072 A | 1/1997 | Handlin, Jr. et al. | |
| 5,612,107 A | 3/1997 | Sangani et al. | |
| 5,631,015 A | 5/1997 | Bezwada et al. | |
| 5,639,831 A * | 6/1997 | Himes | C08F 297/044 525/314 |
| 5,653,992 A | 8/1997 | Bezwada et al. | |
| 5,728,469 A | 3/1998 | Mann et al. | |
| 5,756,585 A | 5/1998 | Teyssie et al. | |
| 5,763,548 A | 6/1998 | Matyjaszewski et al. | |
| 5,789,487 A | 8/1998 | Matyjaszewski et al. | |
| 5,807,937 A | 9/1998 | Matyjaszewski et al. | |
| 5,933,695 A | 8/1999 | Henry et al. | |
| 5,945,491 A | 8/1999 | Matyjaszewski et al. | |
| 6,103,361 A | 8/2000 | Batzar et al. | |
| 6,111,022 A | 8/2000 | Matyjaszewski et al. | |
| 6,111,055 A | 8/2000 | Berger et al. | |
| 6,121,371 A | 9/2000 | Matyjaszewski et al. | |
| 6,124,411 A | 9/2000 | Matyjaszewski et al. | |
| 6,162,882 A | 12/2000 | Matyjaszewski et al. | |
| 6,210,524 B1 | 4/2001 | Josephy | |
| 6,221,399 B1 | 4/2001 | Rolfes et al. | |
| 6,252,014 B1 | 6/2001 | Knauss | |
| 6,336,966 B1 | 1/2002 | Coca et al. | |
| 6,407,187 B1 | 6/2002 | Matyjaszewski et al. | |
| 6,455,623 B1 | 9/2002 | Howard | |
| 6,461,631 B1 | 10/2002 | Dunn et al. | |
| 6,465,091 B1 | 10/2002 | Ou-Yang | |
| 6,476,079 B1 | 11/2002 | Jukarainen et al. | |
| 6,512,060 B1 | 1/2003 | Matyjaszewski et al. | |
| 6,528,080 B2 | 3/2003 | Dunn et al. | |
| 6,538,091 B1 | 3/2003 | Matyjaszewski et al. | |
| 6,541,580 B1 | 4/2003 | Matyjaszewski et al. | |
| 6,555,237 B1 | 4/2003 | Chen et al. | |
| 6,558,805 B2 | 5/2003 | Khadir et al. | |
| 6,624,262 B2 | 9/2003 | Matyjaszewski et al. | |
| 6,624,263 B2 | 9/2003 | Matyjaszewski et al. | |
| 6,626,950 B2 | 9/2003 | Brown et al. | |
| 6,627,314 B2 | 9/2003 | Matyjaszewski et al. | |
| 6,685,957 B1 | 2/2004 | Bezemer et al. | |
| 6,692,770 B2 | 2/2004 | Gustavsson et al. | |
| 6,706,288 B2 | 3/2004 | Gustavsson et al. | |
| 6,759,491 B2 | 7/2004 | Matyjaszewski et al. | |
| 6,764,731 B2 | 7/2004 | Savoca et al. | |
| 6,784,397 B2 | 8/2004 | Li et al. | |
| 6,790,919 B2 | 9/2004 | Matyjaszewski et al. | |
| 6,887,962 B2 | 5/2005 | Matyjaszewski et al. | |
| 6,919,405 B2 | 7/2005 | Kinning et al. | |
| 6,939,505 B2 | 9/2005 | Musso et al. | |
| 7,019,082 B2 | 3/2006 | Matyjaszewski et al. | |
| 7,049,373 B2 | 5/2006 | Matyjaszewski et al. | |
| 7,056,455 B2 | 6/2006 | Matyjaszewski et al. | |
| 7,064,166 B2 | 6/2006 | Matyjaszewski et al. | |
| 7,105,175 B2 | 9/2006 | Schwarz | |
| 7,105,181 B2 | 9/2006 | Gustavsson et al. | |
| 7,125,938 B2 | 10/2006 | Matyjaszewski et al. | |
| 7,153,821 B2 | 12/2006 | Blokzijl et al. | |
| 7,163,697 B2 | 1/2007 | Hanes et al. | |
| 7,173,095 B2 | 2/2007 | Meulenbrugge et al. | |
| 7,186,759 B2 | 3/2007 | Seppala et al. | |
| 7,229,687 B2 | 6/2007 | Kinning et al. | |
| 7,235,261 B2 | 6/2007 | Smith et al. | |
| 7,241,455 B2 | 7/2007 | Richard | |
| 7,316,811 B2 | 1/2008 | Zhao et al. | |
| 7,341,720 B2 | 3/2008 | Stefano | |
| 7,381,418 B2 | 6/2008 | Richard | |
| 7,517,914 B2 | 4/2009 | Richard | |
| 7,537,781 B2 | 5/2009 | Richard | |
| 7,592,021 B2 | 9/2009 | Shankar et al. | |
| 7,612,029 B2 | 11/2009 | Foland et al. | |
| 7,713,539 B2 | 5/2010 | Strickler et al. | |
| 8,173,750 B2 * | 5/2012 | Jakubowski | A61K 8/72 525/244 |
| 8,569,421 B2 * | 10/2013 | Jakubowski | A61K 8/8152 525/244 |
| 8,604,132 B2 * | 12/2013 | Jakubowski | A61K 8/72 525/244 |
| 8,815,971 B2 | 8/2014 | Jakubowski et al. | |
| 8,933,183 B2 | 1/2015 | Kato et al. | |
| 9,382,370 B2 * | 7/2016 | Jakubowski | A61K 8/72 |
| 9,399,694 B2 * | 7/2016 | Jakubowski | A61K 8/8152 |
| 2002/0044976 A1 | 4/2002 | Gustaysson et al. | |
| 2002/0082543 A1 | 6/2002 | Park et al. | |
| 2002/0090398 A1 | 7/2002 | Dunn et al. | |
| 2002/0155309 A1 | 10/2002 | Li et al. | |
| 2002/0155310 A1 | 10/2002 | Li et al. | |
| 2003/0003127 A1 | 1/2003 | Brown et al. | |
| 2003/0004578 A1 | 1/2003 | Brown et al. | |
| 2003/0018154 A1 | 1/2003 | Khadir et al. | |
| 2003/0054185 A1 | 3/2003 | Ottersbach et al. | |
| 2003/0086895 A1 | 5/2003 | Hanes et al. | |
| 2003/0091630 A1 | 5/2003 | Louie-Helm et al. | |
| 2003/0104052 A1 | 6/2003 | Berner et al. | |
| 2003/0133985 A1 | 7/2003 | Louie-Helm et al. | |
| 2003/0138579 A1 | 7/2003 | Savoca et al. | |
| 2003/0152622 A1 | 8/2003 | Louie-Helm et al. | |
| 2003/0153457 A1 | 8/2003 | Nemoto et al. | |
| 2003/0158076 A1 | 8/2003 | Rodrigues | |
| 2003/0158344 A1 | 8/2003 | Rodrigues et al. | |
| 2003/0173720 A1 | 9/2003 | Musso et al. | |
| 2003/0203000 A1 | 10/2003 | Schwarz et al. | |
| 2003/0211167 A1 | 11/2003 | Gustaysson et al. | |
| 2003/0220254 A1 | 11/2003 | Khan et al. | |
| 2003/0235602 A1 | 12/2003 | Schwarz | |
| 2003/0235603 A1 | 12/2003 | Schwarz et al. | |
| 2003/0236513 A1 | 12/2003 | Schwarz et al. | |
| 2003/0236514 A1 | 12/2003 | Schwarz | |
| 2004/0001891 A1 | 1/2004 | Smith et al. | |
| 2004/0006153 A1 | 1/2004 | Seppala et al. | |
| 2004/0023987 A1 | 2/2004 | Hata et al. | |
| 2004/0068078 A1 | 4/2004 | Milbocker | |
| 2004/0086544 A1 | 5/2004 | Bezemer et al. | |
| 2004/0115281 A1 | 6/2004 | Gustavsson et al. | |
| 2004/0126576 A1 | 7/2004 | Kinning et al. | |
| 2004/0156899 A1 | 8/2004 | Louie-Helm et al. | |
| 2004/0161403 A1 | 8/2004 | Zhao et al. | |
| 2004/0171513 A1 | 9/2004 | Blokzijl et al. | |
| 2004/0175406 A1 | 9/2004 | Schwarz | |
| 2004/0185105 A1 | 9/2004 | Berner et al. | |
| 2004/0202691 A1 | 10/2004 | Richard | |
| 2004/0234571 A1 | 11/2004 | Jang | |
| 2005/0025800 A1 | 2/2005 | Tan | |
| 2005/0025801 A1 | 2/2005 | Richard et al. | |
| 2005/0064011 A1 | 3/2005 | Song et al. | |

(56) References Cited

U.S. PATENT DOCUMENTS

| | | |
|---|---|---|
| 2005/0181014 A1 | 8/2005 | Richard |
| 2005/0181015 A1 | 8/2005 | Zhong |
| 2005/0214531 A1 | 9/2005 | Kinning et al. |
| 2005/0233062 A1 | 10/2005 | Hossainy et al. |
| 2005/0244640 A1 | 11/2005 | Riswick et al. |
| 2006/0013849 A1 | 1/2006 | Strickler et al. |
| 2006/0018951 A1 | 1/2006 | Maniar et al. |
| 2006/0024357 A1 | 2/2006 | Carpenter et al. |
| 2006/0051390 A1 | 3/2006 | Schwarz |
| 2006/0068378 A1 | 3/2006 | Mirkin et al. |
| 2006/0121076 A1 | 6/2006 | Ranade et al. |
| 2006/0121085 A1 | 6/2006 | Warren et al. |
| 2006/0147490 A1 | 7/2006 | Bowden |
| 2006/0159619 A1 | 7/2006 | Becker et al. |
| 2006/0165753 A1 | 7/2006 | Richard |
| 2006/0188486 A1 | 8/2006 | Carpenter et al. |
| 2006/0210604 A1 | 9/2006 | Dadey et al. |
| 2006/0222681 A1 | 10/2006 | Richard |
| 2006/0228348 A1 | 10/2006 | Stefano |
| 2007/0003599 A1 | 1/2007 | Schwarz |
| 2007/0020307 A1 | 1/2007 | Zhong et al. |
| 2007/0135532 A1 | 6/2007 | Seppala et al. |
| 2007/0160561 A1 | 7/2007 | Ouali et al. |
| 2007/0212418 A1 | 9/2007 | Ahlheim |
| 2007/0238634 A1 | 10/2007 | Foland et al. |
| 2007/0254010 A1 | 11/2007 | Richard |
| 2007/0260015 A1 | 11/2007 | Stork et al. |
| 2007/0275027 A1 | 11/2007 | Wen et al. |
| 2007/0275080 A1 | 11/2007 | Laulicht et al. |
| 2007/0275082 A1 | 11/2007 | Lee et al. |
| 2007/0280992 A1 | 12/2007 | Margaron et al. |
| 2007/0281031 A1 | 12/2007 | Yang |
| 2007/0299227 A1 | 12/2007 | Gopferich et al. |
| 2007/0299238 A1 | 12/2007 | Gopferich et al. |
| 2007/0299240 A1 | 12/2007 | Gopferich et al. |
| 2008/0112898 A1 | 5/2008 | Schiemann et al. |
| 2008/0114128 A1* | 5/2008 | Destarac ............ C08F 293/005 525/193 |
| 2008/0131395 A1 | 6/2008 | Wellinghoff et al. |
| 2008/0132580 A1 | 6/2008 | Mandavilli et al. |
| 2008/0149348 A1 | 6/2008 | DiFoggio et al. |
| 2008/0226658 A1 | 9/2008 | Stefano |
| 2008/0280037 A1 | 11/2008 | Sheridan et al. |
| 2008/0280086 A1 | 11/2008 | Sheridan et al. |
| 2008/0286333 A1 | 11/2008 | Kangas et al. |
| 2008/0299168 A1 | 12/2008 | Dadey et al. |
| 2008/0311173 A1 | 12/2008 | Schwarz et al. |
| 2009/0087493 A1 | 4/2009 | Dai et al. |
| 2009/0092650 A1 | 4/2009 | Warren et al. |
| 2009/0098079 A1 | 4/2009 | Schiemann et al. |
| 2009/0098183 A1 | 4/2009 | Detamore et al. |
| 2009/0099151 A1 | 4/2009 | Jain et al. |
| 2009/0130172 A1 | 5/2009 | Dankers et al. |
| 2009/0137432 A1 | 5/2009 | Sullivan et al. |
| 2009/0142313 A1 | 6/2009 | Talling et al. |
| 2009/0181094 A1 | 7/2009 | Sheu |
| 2009/0234059 A1* | 9/2009 | Handlin, Jr. .......... C08F 297/04 524/505 |
| 2009/0291106 A1 | 11/2009 | Gopferich et al. |
| 2009/0312505 A1 | 12/2009 | Matyjaszewski et al. |
| 2009/0326645 A1 | 12/2009 | Pacetti et al. |
| 2010/0086597 A1 | 4/2010 | Woo et al. |
| 2010/0120637 A1 | 5/2010 | Bendejacq et al. |
| 2010/0120970 A1 | 5/2010 | Biggs et al. |
| 2010/0273949 A1 | 10/2010 | Jakubowski et al. |
| 2011/0213105 A1 | 9/2011 | Jakubowski et al. |
| 2013/0296495 A1 | 11/2013 | Jakubowski et al. |
| 2014/0024783 A1 | 1/2014 | Jakubowski et al. |

FOREIGN PATENT DOCUMENTS

| | | | |
|---|---|---|---|
| EP | 1197498 A1 | 4/2002 | |
| JP | 2005113086 A | 4/2005 | |
| JP | 2006002032 A | 1/2006 | |
| JP | 2007508401 A | 4/2007 | |
| JP | 2013514431 A | 4/2013 | |
| JP | 2014193398 A | 10/2014 | |
| WO | 2005113031 A2 | 12/2005 | |
| WO | 2005116097 A1 | 12/2005 | |
| WO | WO-2005116097 A1 * | 12/2005 | .......... C08F 293/005 |
| WO | 2010111708 A1 | 9/2010 | |
| WO | 2012020545 A1 | 2/2012 | |

OTHER PUBLICATIONS

Zheng, Genhua et al. "Preparation of Star Polymers Based on Polystyrene or Poly(styrene-b-N-isopropyl acrylamide) and Divinylbenzene Via Reversible Addition-Fragmentation Chain Transfer Polymerization," Polymer46 (2005) 28022810.

Ali, Monzur et al. "Synthetic Approaches to Uniform Polymers" Advanced Drug Delivery Reviews 58 (2006) 16711687.

Bouilhac, Cecile et al. "Benzophenone-Functionalized, Starlike Polystyrenes as Organic Supports for a Tridentate Bis(imino)pyridinyliron/Trimethylaluminum Catalytic System for Ethylene Polymerization," J. Polm. Sci. Part A: Polym. Chem. 44 (2006) 6997-7007.

Burke, Sandra E. et al. "Zotarolimus (ABT-578) Eluting Stents" Advanced Drug Delivery Reviews 58 (2006) 437-446.

Daugherty, Ann L. et al. "Formulation and Delivery Issues for Monoclonal Antibody Therapeutics" Adv. Drug Deliv. Rev. 58 (2006) 686-706.

Gao, Haifeng et al. "Characterization of Linear and 3-Arm Star Block Copolymers by Liquid Chromatography at Critical Conditions," Macromol. Chem. Phys. 207 (2006) 1709-1717.

Gao, Haifeng et al. "Low Polydispersity Star Polymers via Cross-Linking Macromonomers by ATRP," J. Am. Chem. Soc. 128 (2006) 15111-15113.

Gao, Haifeng et al. "Structural Control in ATRP Synthesis of Star Polymers Using the Arm-First Method," Macromolecules 39:9 (2006) 3154-3160.

Hadjichristidis, Nikos et al. "Macromolecular Architectures by Living and Controlled/Living Polymerizations," Prog. Polym. Sci. 31 (2006) 1068-1132.

Jones, M.C. et al. "Self-Assembled Nanocages for Hydrophilic Guest Molecules," J. Am. Chem. Soc. 128:45 (Oct. 21, 2006) 14599-14605.

Kafouris, Demetris et al. "Synthesis and Characterization of Star Polymers and Cross-Linked Star Polymer Model Networks with Cores Based on an Asymmetric, Hydrolyzable Dimethacrylate Cross-Linker," Chem. Mater. 18 (2006) 85-93.

Kreutzer, Georg et al. "Water-Soluble, Unimolecular Containers Based on Amphiphilic Multiarm Star Block Copolymers," Macromolecules 39 (2006) 4507-4516.

Lee, Cameron C. et al. "A Single Dose of Doxorubicin-Functionalized Bow-Tie Dendrimer Cures Mice Bearing C-26 Colon Carcinomas" PNAS 103 :45 (2006) 16649-16654.

Lshizu, Koji et al. "Synthesis of Amphiphilic Star Block Copolymers Via Diethyldithiocarbamate-Mediated Living Radical Polymerization," J. Polm_ Sci. Part A: Polym. Chem. 44 (2006) 3321-3327.

McCarthy, Patrick et al. "Grafting Chromatographic Stationary Phase Substrates by Atom Transfer Radical Polymerization" Controlled/Living Radical Polymerization, Chapter 18, ACS Symposium Series 944 (2006) 252-268.

McCormick, Charles L. et al. "Synthetic Routes to Stimuli-Responsive Micelles, Vesicles, and Surfaces via Controlled/Living Radical Polymerization" Polymer Reviews 46 (2006) 421-443.

Oh, Jung K. et al. "Inverse Miniemulsion ATRP: A New Method for Synthesis and Functionalization of Well-Defined Water-Soluble/ Cross-Linked Polymeric Particles" J. Am. Chem. Soc. 128 (2006) 5578-5584.

Rosenberg, Amy S. "Effects of Protein Aggregates: An Immunologic Perspective" AAPS J. 8:3 (2006) E501-E507.

Taton, Daniel et al. "Controlled Polymerizations as Tools for the Design of Star-Like and Dendrimer-Like Polymers," Po/ym. Int. 55 (2006) 1138-1145.

(56) References Cited

OTHER PUBLICATIONS

Themistou, Efrosyni et al. "Synthesis and Characterization of Polymer Networks and Star Polymers Containing a Novel, Hydrolyzable Acetal-Based Dimethacrylate Cross-Linker," Macromolecules 39 (2006) 73-80.

Tsarevsky, Nicolay V. et al. "Controlled Synthesis of Polymers with Ionic or Ionizable Groups Using Atom Transfer Radical Polymerization" Polyelectrolytes and Polyzwitterions, Chapter 5, ACS Symposium Series 937 (2006) 79-94.

Wiltshire, James T. et al. "Selectively Degradable Core Cross-Linked Star Polymers," Macromolecules 39 (2006) 9018-9027.

Chong, Y. K et al. "Thiocarbonylthio End Group Removal from RAFT-Synthesized Polymers by Radical-Induced Reduction," Macromolecules 40:13 (May 22, 2007) 4446-4455.

Connal, Luke A. et al. "Synthesis of Dendron Functionalized Core Cross-Linked Star Polymers," Macromolecules 40 (2007) 7855-7863.

Gao, Haifeng et al. "Arm-First Method as a Simple and General Method for Synthesis of Miktoarm Star Copolymers," J. Am. Chem. Soc. 129:38 (2007) 11828-11834.

Gao, Haifeng et al. "Low-Polydispersity Star Polymers with Core Functionality by Cross-Linking Macromonomers Using Functional ATRP Initiators," Macromolecules 40 (2007) 399-401.

Hietala, Sami et al. "Synthesis and Rheological Properties of an Associative Star Polymer in Aqueous Solutions," Polymer 48 (2007) 4087-4096.

Tsarevsky, Nicolay V. et al. "Graft Copolymers by a Combination of ATRP and Two Different Consecutive Click Reactions" Macromolecules 40:13 (2007) 4439-4445.

Adkins, Chinessa T. et al. "Synthesis of Star Polymer Architectures with Site-Isolated Chromophore Cores," Macromolecules 41 (2008) 3472-3480.

Allen, Barry J. "Clinical Trials of Targeted Alpha Therapy for Cancer" Rev.Recent Clin.Trials 3:3 (2008) 185-191.

Blencowe, Anton et al. "Synthesis of Buckminsterfullerene Ceo Functionalised Core Cross-Linked Star Polymers," Polymer 49 (2008) 825-830.

Braunecker, W. A. et al. Progress in Polymer Science 33 (2008) 165.

Chari, Ravi V. J. "Targeted Cancer Therapy : Conferring Specificity to Cytotoxic Drugs" Acc. Chem. Res. 41:1 (2008) 98-107.

Fukukawa, Ken-Ichi et al. "Synthesis and Characterization of Core-Shell Star Copolymers for In Vivo PET Imaging Applications," Biomacromolecules 9 (2008) 1329-1339.

Gao, Haifeng et al. "Synthesis of Low-Polydispersity Miktoarm Star Copolymers Via a Simple 'Arm-First' Method: Macromonomers as Arm Precursors," Macromolecules 41:12 (2008) 4250-4257.

Kelly, Marcus P. et al. "Tumor Targeting by a Multivalent Single-Chain Fv (scFv) Anti-Lewis Y Antibody Construct" Cancer. Biother. Radiopharm. 23:4 (2008) 411-424.

Moad, Graeme et al. "Radical Addition-Fragmentation Chemistry in Polymer Synthesis" Polymer 49 (2008) 10791131.

Sciannamea, Valerie et al. "In-Situ Nitroxide-Mediated Radical Polymerization (NMP) Processes: Their Understanding and Optimization" Chem. Rev. 108:3 (2008) 1104-1126.

Spiniello, Marisa et al. "Synthesis and Characterization of Fluorescently Labeled Core Cross-Linked Star Polymers," J. Polm. Sci. Part A: Polym. Chem. 46 (2008) 2422-2432.

York, Adam W. et al. "Advances in the Synthesis of Amphiphilic Block Copolymers via RAFT Polymerization: Stimuli-Responsive Drug and Gene Delivery" Advanced Drug Delivery Reviews 60 (2008) 1018-1036.

Andrzej Plichta, et al., "ICAR ATRP of Styrene and Methyl Methacrylate with Ru(Cp''')Cl(PPh3)2" , Macromolecules, 2009, vol. 42, 2330-2332.

Gao, Haifeng et al. "Synthesis of Functional Polymers with Controlled Architecture by CRP of Monomers in the Presence of Cross-Linkers: From Stars to Gels," Progress in Polymer Science 34:4 (2009) 317-350.

Hietala, Sami et al. "Rheological Properties of Associative Star Polymers in Aqueous Solutions: Effect of Hydrophone Length and Polymer Topology," Macromolecules 42 (2009) 1726-1732.

Bencherif, Sidi A. et al. "Cell-Adhesive Star Polymers Prepared by ATRP," Biomacromolecules 10 (2010) 1795-1803.

Gao, Haifeng et al. "Modular Approaches to Star and Miktoarm Star Polymers by ATRP of Cross-Linkers," Macromol. Symp. 291-292 (2010) 12-16.

Li, Wenwen et al. "Uniform PEO Star Polymers Synthesized in Water via Free Radical Polymerization or Atom Transfer Radical Polymerization," Macromol. Rapid Commun. 31 (2010) 74-81.

Terashima, Takaya et al. "In Situ and Time-Resolved Small-Angle Neutron Scattering Observation of Star Polymer Formation via Arm-Linking Reaction in Ruthenium-Catalyzed Living Radical Polymerization," Macromolecules 43 (2010) 8218-8232.

Van Camp, Wim et al. "Effect of Crosslinker Multiplicity on the Gel Point in ATRP," J. Polym. Sci., Part A: Polymer Chemistry 48 (2010) 2016-2023.

Goh, Tor Kit et al. "Highly Efficient Synthesis of Low Polydispersity Corss Cross-Linked Star Polymers by Ru-Catalyzed Living Radical Polymerization," Macromol. Rapid Commun. 32 (2011) 456-461.

Koda, Yuta et al. "Fluorinated Microgel-Core Star Polymers as Fluorous Compartments for Molecular Recognition," Macromolecules 44 (2011) 4574-4578.

Blainey, J. D. "The Renal Excretion of Higher Molecular Weight Substances" Enzymes in Urine and Kidney Proceedings: Curr. Probl. Clin. Biochem. 2 (1968) 85-100.

Bi, Le-Khac et al. "Synthesis and Properties of Block Copolymers. 3. Polystyrene-Polydiene Star Block Copolymers," Macromolecules 9:5 (Sep.-Oct. 1976) 732-742.

Ishizu, Koji et al. "Synthesis of Star Polymers by Organized Polymerization of Macromonomers," Polymer 36:21 (1995) 4155-4157.

Wang, Jin-Shan et al. "Controlled/'Living' Radical Polymerization. Atom Transfer Radical Polymerization in the Presence of Transition-Metal Complexes" J. Am. Chem. Soc. 117 (1995) 5614-5615.

Matyjaszewski, Krzysztof et al. "Synthesis of Well-Defined Azido and Amino End-Functionalized Polystyrene by Atom Transfer Radical Polymerization" Macromol. Rapid Commun. 18 (1997) 1057-1066.

Beers, Kathryn L. et al. "The Synthesis of Densely Grafted Copolymers by Atom Transfer Radical Polymerization" Macromolecules 31:26 (1998) 9413-9415.

Beers, Kathryn L. et al. "Atom Transfer Radical Polymerization of 2-Hydroxyethyl Methacrylate" Macromolecules 32 :18 (1999) 5772-5776.

Hadjichristidis, Nikos "Synthesis of Miktoarm Star (p-Star) Polymers," J. Polym. Sci, Part A: Polym. Chem. 37 (1999) 857-871.

Xia, Jianhui et al. "Synthesis of Star-Shaped Polystyrene by Atom Transfer Radical Polymerization Using an 'Arm First' Approach," Macromolecules 32 (1999) 4482-4484.

Held, Daniela et al. "Synthesis and Solution Properties of Star-Shaped Poly(tert-butyl acrylate)," Macromol. Symp. 157 (2000) 225-237.

Zhang, Xuan et al. "End-Functional Poly(tert-butyl acrylate) Star Polymers by Controlled Radical Polymerization," Macromolecules 33 (2000) 2340-2345.

Baek, Kyung-Youl et al. "Core-Functionalized Star Polymers by Transition Metal-Catalyzed Living Radical Polymerization. 1. Synthesis and Characterization of Star Polymers with PMMA Arms and Amide Cores," Macromolecules 34 (2001) 7629-7635.

Baek, Kyung-Youl et al. "Star-Shaped Polymers by Metal-Catalyzed Living Radical Polymerization. 1. Design of Ru(II)-Based Systems and Divinyl Linking Agents," Macromolecules 34 (2001) 215-221.

Bosman, Anton W. et al. "High-Throughput Synthesis of Nanoscale Materials: Structural Optimization of Functionalized One-Step Star Polymers," J. Am. Chem. Soc. 123 (2001) 6461-6462.

Matyjaszewski, Krzysztof et al. "Atom Transfer Radical Polymerization" Chem. Rev. 101:9 (2001) 2921-2990.

Pasquale, Anthony J. et al. "Synthesis of Star-Shaped Polystyrenes via Nitroxide-Mediated Stable Free-Radical Polymerization," J. Polm. Sci. Part A: Polym. Chem. 39 (2001) 216-223.

(56) References Cited

OTHER PUBLICATIONS

Tsoukatos, Thodoris et al. "Star-Branched Polystyrenes by Nitroxide Living Free-Radical Polymerization," J. Rolm. Sci. Part A: Polym. Chem. 39 (2001) 320-325.

Baek, Kyung-Youl et al. "Star Poly(methyl methacrylate) with End-Functionalized Arm Chains by Ruthenium-Catalyzed Living Radical Polymerization," J. Polm. Sci. Part A: Polym. Chem. 40 (2002) 1972-1982.

Baek, Kyung-Youl et al. "Synthesis of Star-Shaped Copolymers with Methyl Methacrylate and n-Butyl Methacrylate by Metal-Catalyzed Living Radical Polymerization: Block and Random Copolymer Arms and Microgel Cores," J. Polm. Sci. Part A: Polym. Chem. 40 (2002) 633-641.

Furukawa, Taiichi et al. "Synthesis and Characterization of Poly-(ethylene oxide) Star Polymers Possessing a Tertiary Amino Group at Each Arm End by Organized Polymerization Using Macromonomers," Journal of Colloid and Interface Science 253 (2002) 465-469.

Narumi, Atsushi et al. "Glycoconjugated Polymer. 3. Synthesis and Amphiphilic Property of Core-Glycoconjugated Star-Shaped Polystyrene," Macromolecules 35 (2002) 699-705.

Tsarevsky, Nicolay V. et al. "Reversible Redox Cleavage/Coupling of Polystyrene with Disulfide or Thiol Groups Prepared by Atom Transfer Radical Polymerization" Macromolecules 35 (2002) 9009-9014.

Bosman, Anton W. et al. "A Modular Approach Toward Functionalized Three-Dimensional Macromolecules: From Synthetic Concepts to Practical Applications," J. Am. Chem. Soc. 125 (2003) 715-728.

Matyjaszewski, Krzysztof "The Synthesis of Functional Star Copolymers as an Illustration of the Importance of Controlling Polymer Structures in the Design of New Materials," Polym. Int. 52 (2003) 1559-1565.

Moad, Graeme et al. "Synthesis of Novel Architectures by Radical Polymerization with Reversible Addition Fragmentation Chain Transfer (RAFT Polymerization)," Macromol. Symp. 192 (2003) 1-12.

Terashima, Takaya et al. "Polymer Catalysts from Polymerization Catalysts: Direct Encapsulation of Metal Catalyst into Star Polymer Core During Metal-Catalyzed Living Radical Polymerization," J. Am. Chem. Soc. 125 (2003) 52885289.

Yoo, Mikyong et al. "Photophysical Characterization of Conformational Rearrangements for Amphiphilic 6-Arm Star Block Copolymers in Selective Solvent Mixtures," Macromolecules 36:1 (2003) 268-271.

Bontempo, Debora et al. "Cysteine-Reactive Polymers Synthesized by Atom Transfer Radical Polymerization for Conjugation to Proteins" J. Am. Chem. Soc. 126 :47 (2004) 15372-15373.

Du, Jianzhong et al. "PCL Star Polymer, PCL-PS Heteroarm Star Polymer by ATRP, and Core-Carboxylated PS Star Polymer Thereof," Macromolecules 37 (2004) 3588-3594.

Du, Jianzhong et al. "Preparation of Poly(ethylene oxide) Star Polymers and Poly(ethylene oxide)-Polystyrene Heteroarm Star Polymers by Atom Transfer Radical Polymerization," J. Polm. Sci. Part A: Polym. Chem. 42 (2004) 2263-2271.

Froidevaux, Sylvie et al. "A Gallium-Labeled DOTA-a-Melanocyte-Stimulating Hormone Analog for PET Imaging of Melanoma Metastases" J Nucl Med. 45:1 (2004) 116-123.

Jankova, K. et al. "Novel Fluorinated Block Copolymer Architectures Fuelled by Atom Transfer Radical Polymerization," Journal of Fluorine Chemistry 126:2 (Dec. 10, 2004) 241-250.

Pan, Dipanjan et al. "Shell Cross-Linked Nanoparticles Designed to Target Angiogenic Blood Vessels via 0v133 Receptor-Ligand Interactions" Macromolecules 37:19 (2004) 7109-7115.

Themistou, Efrosyni et al. "Synthesis and Characterization of Star Polymers and Cross-Linked Star Polymer Model Networks Containing a Novel, Silicon-Based, Hydrolyzable Cross-Linker," Macromolecules 37 (2004) 6734-6743.

Tsarevsky, Nicolay V. et al. "Deactivation Efficiency and Degree of Control Over Polymerization in ATRP in Protic Solvents" Macromolecules 37 (2004) 9768-9778.

Bouilhac, Cecile et al. "Functionalized Star-Like Polystyrenes as Organic Supports of a Tridentate Bis(imino) pyridinyliron/Aluminic Derivative Catalytic System for Ethylene Polymerization," Macromol. Rapid Commun. 26 (2005) 1619-1625.

Ferrari, Mauro, "Cancer Nanotechnology : Opportunities and Challenges" Nature Reviews Cancer 5 (2005) 161-171.

Furukawa, Taiichi et al. "Synthesis and Viscoelastic Behavior of Multiarm Star Polyelectrolytes," Macromolecules 38 (2005) 2911-2917.

Gao, Haifeng et al. "Synthesis of Degradable Miktoarm Star Copolymers via Atom Transfer Radical Polymerization," Macromolecules 38:14 (2005) 5995-6004.

Hamann, Philip R. et al. "A Calicheamicin Conjugate with a Fully Humanized Anti-MUC1 Antibody Shows Potent Antitumor Effects in Breast and Ovarian Tumor Xenografts" Bioconjugate Chem. 16 (2005) 354-360.

Huang, Jinyu et al. "Synthesis and Characterization of Copolymers of 5,6-benzo-2-methylene-1,3-dioxepane and n-butyl acrylate" Polymer 46 (2005) 11698-11706.

Kowalczuk-Bleja, A. et al. "Core-Shell Polyacrylate and Polystyrene-Block-Polyacrylate Stars," Polymer46:19 (2005) 8555-8564.

Lee, Cameron C. et al. "Designing Dendrimers for Biological Applications" Nature Biotech. 23 :12 (2005) 1517-1526.

Lee, Hyung-Jae et al. "Controlled Anionic Synthesis of Star-Shaped Polystyrene by the Incremental Additional of Divinylbenzene," J. Polm. Sci. Part A: Polym. Chem. 43 (2005) 870-878.

Liu, Jun et al. "Reversible Self-Association Increases the Viscosity of a Concentrated Monoclonal Antibody in Aqueous Solution" J Pharm Sci. 94:9 (2005) 1928-1940.

Narumi, Atsushi et al. "Star-Shaped Polystyrenes with Glycoconjugated Periphery and Interior: Synthesis and Entrapment of Hydrophilic Molecule," J. Polm. Sci. Pad A: Polym. Chem. 43 (2005) 4373-4381.

Polak's, Paul "Arming Antibodies for Cancer Therapy" Current Opinion in Pharmacology 5 (2005) 382-387.

Rosi, Nathaniel L. et al. "Nanostructures in Biodiagnostics" Chem Rev. 105 (2005) 1547-1562.

Shire, Steven J. et al. "Challenges in the Development of High Protein Concentration Formulations" J. Pharm. Sci. 93:6 (2005) 1390-1402.

Wang, Fei et al. "Synthesis and Evaluation of a Star Amphiphilic Block Copolymer from Poly(C-caprolactone) and Poly(ethylene glycol) as a Potential Drug Delivery Carrier," Bioconjugate Chem. 16 (2005) 397-405.

\* cited by examiner

A  B

OIL SOLUBLE RHEOLOGY MODIFYING STAR MACROMOLECULES

CROSS REFERENCE TO RELATED APPLICATIONS

This application is a continuation of U.S. application Ser. No. 14/036,993, filed Sep. 25, 2013, which is a continuation of U.S. application Ser. No. 12/799,411, filed Apr. 23, 2010, now U.S. Pat. No. 8,569,421, which further claims priority under 35 USC 119(e) to U.S. Provisional Application No. 61/214,397, filed Apr. 23, 2009. The foregoing related applications, in their entirety, are incorporated herein by reference.

FIELD OF THE INVENTION

The present invention relates to multi-arm star macromolecules which are used as rheology modifiers, including use in the cosmetic, personal care and home care compositions.

BACKGROUND AND PRIOR ART

Most personal care products on the market contain many types of polymers that vary by structure, chemistry, and raw material source (synthetic or natural) that are combined to provide products with many different desired functions. One class of polymer additives is targeted at altering or modifying the rheological properties of the product that are very important for consumer appeal. Often, additives that provide sufficient viscosity are needed, especially for those formulations where the viscosity without additives is close to that of the pure solvent (water). However, merely increasing viscosity is not sufficient, and in reality, the modifiers should be selected to provide certain desired rheological properties for the formulation that depend on its nature, the mode of delivery, type of flow, and the aesthetic appeal of final application. Typically, low molecular weight surfactants are used to modify rheological properties but they have to be used at large concentrations. Resulting in relatively high cost, and an adverse impact on the environment (e.g., water pollution).

The thickeners used in cosmetic and body care preparations have to meet stringent requirements. First and foremost, they have to show high compatibility and also—if possible—biodegradability so that many substances have to be ruled out from the outset for use in cosmetics. In addition, they should be universally useable in aqueous, emulsoidal, alcoholic and oil-containing bases, be readily processable and lead to a rheology which enables the product to be easily applied so that the preparations can be removed and distributed under clean and simple conditions.

Thickeners that are designed molecular level to provide the desired properties would be expected to be compatible with many other auxiliaries, more particularly with salts and surfactants. The thickener itself and the other auxiliaries should also lend themselves to ready incorporation into the formulation. The thickened preparations are also expected to show stable rheology and an unchanging physical and chemical quality even in the event of long-term storage and changes in pH and temperature. Finally, the thickeners should be inexpensive to produce without causing significant environmental pollution.

In view of this complex requirement profile, it is clear why, even today, there is still a demand for new thickeners in the cosmetics field.

SUMMARY OF THE INVENTION

Accordingly, in one aspect the invention provides a polymer composition comprising star macromolecules, each star macromolecule having a core and five or more arms, wherein the number of arms within a star macromolecule varies across the composition of star molecules; the arms on a star are covalently attached to the core of the star; each arm comprises one or more (co)polymer segments; and at least one arm and/or at least one segment exhibits a different solubility from at least one other arm or one other segment, respectively, in a reference liquid of interest The use of the polymer composition in personal care products and homoe care products is also provided.

BRIEF DESCRIPTION OF THE DRAWINGS

The features and advantages of the present invention may be better understood by reference to the accompanying Figures, in which.

DETAILED DESCRIPTION OF THE INVENTION

It must be noted that, as used in this specification, examples and the appended claims, the singular forms "a,"

"and," and "the" include plural referents unless the context clearly dictates otherwise. Thus, for example, reference to "a polymer" may include more than one polymer. The term (co)polymer indicates that the polymer or polymer segment can comprise a homopolymer or a copolymer comprising two or more monomers distributed along the polymer backbone of polymer segment in a random, statistical, alternating or gradient fashion.

Unless otherwise indicated, all numbers expressing quantities of ingredients, time, temperatures, and so forth used in the present specification and claims are to be understood as being modified in all instances by the term "about." Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, may inherently contain certain errors necessarily resulting from the standard deviation found in their respective testing measurements.

It is to be understood that this invention is not limited to specific compositions, components or process steps disclosed herein, as such may vary. It is also to be understood that the terminology used herein is for the purpose of describing particular embodiments only, and is not intended to be limiting.

Any numerical range recited herein is intended to include all sub-ranges subsumed therein.

Structure of the Polymer Composition

Figure 1:
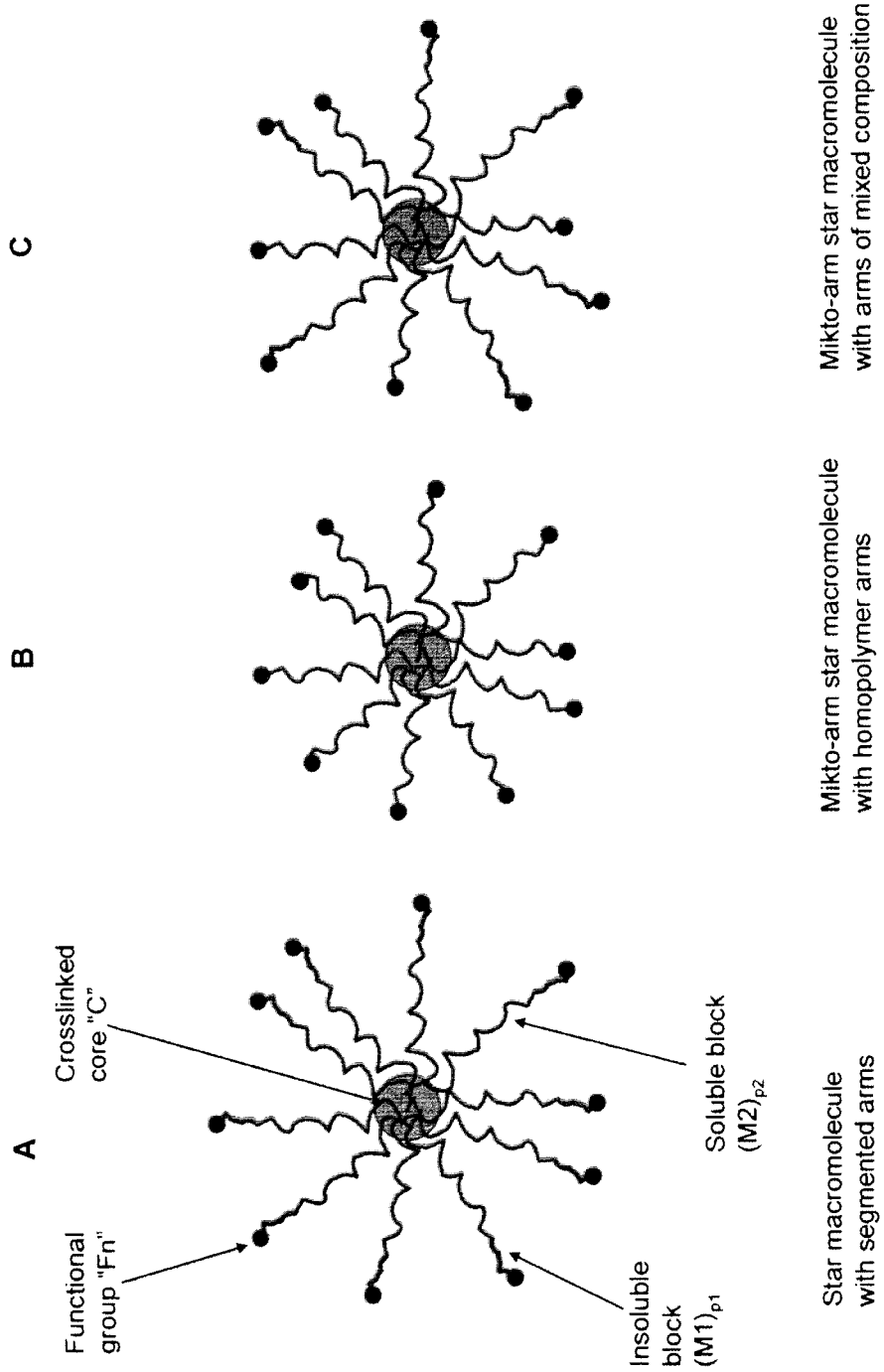
FIG. 1: Illustration of the structure of a segmented homo-arm star macromolecule and two different types of mikto-arm star macromolecules.

The polymer composition of the invention comprises a multi-arm star macromolecule which is shown schematically in FIG. 1

In one embodiment, the arms in a star macromolecule are comprised of two or more (co)polymer segments selected to modify the rheology of the reference liquid of interest. The star macromolecule structure is represented by the following formula $[F-(M1)_{p1}-(M2)_{p2}]_n-C$ wherein i. $[F-(M1)_{p1}-(M2)_{p2}]$ represents an arm comprised of a segmented (co)polymer chain wherein each (co)polymer segment, ii. $(M1)_{p1}$- and $(M2)_{p2}$- are compositionally distinct adjacent (co)polymer segments where each segment is comprised of one or more monomers with homo, random, gradient or block (co)polymer structure and where p1 and p2 represent the degree of polymerization of each copolymer segment, iii. F— represents an optionally functional group or mixture of functional groups present on the arm chain-end, iv. $(M1)_{p1}$ is not soluble or not fully soluble in the reference liquid of interest, v. $(M2)_{p2}$ is soluble or mostly soluble in the reference liquid of interest, vi. and C represents the crosslinked core of the star macromolecule which is comprised of crosslinker (Mx), crosslinker (Mx) and monomer (My), crosslinker (Mx) and (M2), or a mixture of (Mx), (My) and (M2), and vii. n represents the average number of arms covalently attached to the core of the star macromolecule.

In another embodiment, the star macromolecule structure can be represented by the following formula, $$[F-(M1)_{p1}-(M2)_{p2}]_n-C-[(M3)_{p3}-F]_m \text{ wherein}$$

i. $[F-(M1)_{p1}-(M2)_{p2}]$ represents an arm comprised of a segmented (co)polymer chain, ii. $(M1)_{p1}$- and $(M2)_{p2}$- are compositionally distinct adjacent (co)polymer segments where each segment is comprised of one or more monomers with homo, random, gradient or block (co)polymer structure and where p1 and p2 represent the degree of polymerization of each copolymer segment, iii. F— represents an optionally functional group or mixture of functional groups present on the arm chain-end, iv. $(M1)_{p1}$ is not soluble or not fully soluble in the reference liquid of interest, v. $(M2)_{p2}$ is soluble or mostly soluble in the reference liquid of interest, vi. and C represents the crosslinked core of the star macromolecule which is comprised of crosslinker (Mx), crosslinker (Mx) and monomer (My), crosslinker (Mx) and (M2), or a mixture of (Mx), (My) and (M2), and vii. n represents the average number of arms covalently attached to the core of the star macromolecule.

viii. $(M3)_{p3}$ is a (co)polymer segment which is comprised of one or more monomers with homo, random, gradient or block (co)polymer structure with a degree of polymerization p3 and ix. m is the number of $(M3)_3$ (co)polymer arms covalently attached to the core, x. $(M3)_{p3}$ is soluble or mostly soluble in the reference liquid of interest and xi. M2 and M3 can be comprised of the same or different (co)monomers.

In a further embodiment, polymer composition comprises star macromolecules in which the structure of a star can be represented by the following formula, $$[F-(M1)_{p1}]_s-C-[(M3)_{p3}-F]_m \text{ wherein}$$

i. $[F-(M1)_{p1}-(M2)_{p2}]$ represents an arm comprised of a segmented (co)polymer chain, ii. $(M1)_{p1}$- is a (co)polymer segment where each segment is comprised of one or more monomers with homo, random, gradient or block (co)polymer structure with a degree of polymerization p1, iii. F— represents an optionally functional group or mixture of functional groups present on the arm chain-end, iv. $(M1)_{p1}$ is not soluble or not fully soluble in the reference liquid of interest, v. C represents the crosslinked core of the star macromolecule which is comprised of crosslinker (Mx), crosslinker (Mx) and monomer (My), crosslinker (Mx) and (M2), or a mixture of (Mx), (My) and (M2), and vi. $(M3)_{p3}$ is a (co)polymer segment which is comprised of one or more monomers with homo, random, gradient or block (co)polymer structure with a degree of polymerization p3 and vii. $(M3)_{p3}$ is soluble or mostly soluble in the reference liquid of interest and viii. m is the number of $(M3)_3$ (co)polymer arms covalently attached to the core, and ix. s is the average number of $(M1)_{p1}$ (co)polymer arms covalently attached to the core.

In the polymer composition, the number of arms on any particular star varies across the population of star macromolecules in each composition, due to the synthetic process used for the synthesis of the composition. This process is called "arm first" method and is described in details herein below. Due to variation in the number of arms in star macromolecules, the number of arms n, m and s are referred as an average number of arms.

Star macromolecules with a single peak in the GPC curve with a polydispersity index (PM) above 1.0 and below 2.5 is preferred.

As used herein, the term "reference liquid of interest" means the liquid to which the polymer composition will be added. Suitable examples of reference liquids include, but are not limited to, water, oil or mixture thereof or water with additives which include but are not limited to; surfactants, oils, fats and waxes, emulsifiers, silicone compounds, UV protectors, antioxidants, various water soluble substances, biogenic agents, deodorants, odor absorbers, antiperspirants, and germ and enzyme inhibitors. Such agents are disclosed in U.S. Pat. Nos. 6,663,855 and 7,318,929 and are herein incorporated by reference to provide definitions for those terms.

The arms of the star can possess the same composition or be different (e.g. star macromolecule with formula (1) vs. (2) or (3), these star are shown in FIG. 1). The difference can be in composition or molecular weight or both (e.g. different monomer units M1, M2, M3 and/or different degree of polymerization p1, p2, p3).

Term "(co)polymer" is defined as a polymer derived from two or more monomeric species (monomer units)

More preferred specific monomer units as a building blocks of M1, M2, M3 and My include those selected from protected and unprotected acrylic acid, methacrylic acid, ethacrylic acid, methyl acrylate, ethyl acrylate, .alpha.-butyl acrylate, iso-butyl acrylate, t-butyl acrylate, 2-ethylhexyl acrylate, decyl acrylate, octyl acrylate, methyl methacrylate, ethyl methacrylate, n-butyl methacrylate, iso-butyl methacrylate, t-butyl methacrylate, 2-ethylhexyl methacrylate, decyl methacrylate, methyl ethacrylate, ethyl ethacrylate, n-butyl ethacrylate, iso-butyl ethacrylate, t-butyl ethacrylate, 2-ethylhexyl ethacrylate, decyl ethacrylate, 2,3-dihydroxypropyl acrylate, 2,3-dihydroxypropyl methacrylate, 2-hydroxyethyl acrylate, 2-hydroxypropyl acrylate, hydroxypropyl methacrylate, glyceryl monoacrylate, glyceryl monoethacrylate, glycidyl methacrylate, glycidyl acrylate, acrylamide, methacrylamide, ethacrylamide, N-methyl acrylamide, N,N-dimethyl acrylamide, N,N-dimethyl methacrylamide, N-ethyl acrylamide, N-isopropyl acrylamide, N-butyl acrylamide, N-t-butyl acrylamide, N,N-di-n-butyl acrylamide, N,N-diethylacrylamide, N-octyl acrylamide, N-octadecyl acrylamide, N,N-diethylacrylamide, N-phenyl acrylamide, N-methyl methacrylamide, N-ethyl methacrylamide, N-dodecyl methacrylamide, N,N-dimethylaminoethyl acrylamide, quaternised N,N-dimethylaminoethyl acrylamide, N,N-dimethylaminoethyl methacrylamide, quaternised N,N-dimethylaminoethyl methacrylamide, N,N-dimethylaminoethyl acrylate, N,N-dimethylaminoethyl methacrylate, quaternised N,N-dimethyl-aminoethyl acrylate, quaternised N,N-dimethylaminoethyl methacrylate, 2-hydroxyethyl acrylate, 2-hydroxyethyl methacrylate, 2-hydroxyethyl ethacrylate, glyceryl acrylate, 2-methoxyethyl acrylate, 2-methoxyethyl methacrylate, 2-methoxyethyl ethacrylate, 2-ethoxyethyl acrylate, 2-ethoxyethyl methacrylate, 2-ethoxyethyl ethacrylate, maleic acid, maleic anhydride and its half esters, fumaric acid, itaconic acid, itaconic anhydride and its half esters, crotonic acid, angelic acid, diallyldimethyl ammonium chloride, vinyl pyrrolidone vinyl imidazole, methyl vinyl ether, methyl vinyl ketone, maleimide, vinyl pyridine, vinyl pyridine-N-oxide, vinyl furan, styrene sulphonic acid and its salts, allyl alcohol, allyl citrate, allyl tartrate, vinyl acetate, vinyl alcohol, vinyl caprolactam, vinyl acetamide, vinyl formamide and mixtures thereof.

Even more preferred monomer units as a building parts of M1, M2, M3 and My are those selected from methyl acrylate, methyl methacrylate, methyl ethacrylate, ethyl acrylate, ethyl methacrylate, ethyl ethacrylate, n-butyl acrylate, n-butyl methacrylate, n-butyl ethacrylate, 2-ethylhexyl acrylate, 2-ethylhexyl methacrylate, 2-ethylhexyl ethacrylate, N-octyl acrylamide, 2-methoxyethyl acrylate, 2-hydroxyethyl acrylate, N,N-dimethylaminoethyl acrylate, N,N-dimethylaminoethyl methacrylate, acrylic acid, methacrylic acid, N-t-butylacrylamide, N-sec-butylacrylamide, N,N-dimethylacrylamide, N,N-dibutylacrylamide, N,N-dihydroxyethyllacrylamide 2-hydroxyethyl acrylate, 2-hydroxyethyl methacrylate, benzyl acrylate, 4-butoxycarbonylphenyl acrylate, butyl acrylate, 4-cyanobutyl acrylate, cyclohexyl acrylate, dodecyl acrylate, 2-ethylhexyl acrylate, heptyl acrylate, iso-butyl acrylate, 3-methoxybutyl acrylate, 3-methoxypropyl acrylate, methyl acrylate, N-butyl acrylamide, N,N-dibutyl acrylamide, ethyl acrylate, methoxyethyl acrylate, hydroxyethyl acrylate, diethyleneglycolethyl acrylate, styrene (optionally substituted with one or more $C_1$-$C_{12}$ straight or branched chain alkyl groups), alpha-methylstyrene, t-butylstyrene, p-methylstyrene, and mixtures thereof.

All monomer units within the arms are connected with C—C covalent bonds. This makes them hard to degrade so that the star macromolecule can perform as efficient thickening agent in a harsh environment (very high/low pH or in the presence of strong oxidizing agents).

"C" represents the crosslinked core of the star macromolecule which is comprised of crosslinker (Mx), crosslinker (Mx) and monomer (My), crosslinker (Mx) and (M2), or a mixture of (Mx), (My) and (M2).

Suitable crosslinkers (Mx) encompass all of the compounds which are capable, under the polymerization conditions, of bringing about crosslinking. These include but are not limited di-, tri-, tetra-functional (meth)acrylates, di-, tri- and tetra-functional styrenes and other multi- or poly-functional crosslinkers.

Some examples of the crosslinking agents may include but are not limited to 1,2-divinylbenzene, 1,3-divinylbenzene and 1,4-divinylbenzene, 1,2-ethanediol di(meth)acrylate, 1,3-propanediol di(meth)acrylate, 1,4butanediol di(meth)acrylate, 1,5-hexanediol di(meth)acrylate, divinylbenzene, ethyleneglycol di(meth)acrylate, propyleneglycol di(meth)acrylate, butyleneglycol di(meth)acrylate, triethyleneglycol di(meth)acrylate, polyethyleneglycol di(meth)acrylate, polypropyleneglycol di(meth)acrylate, polybutyleneglycol di(meth)acrylate, and allyl(meth)acrylate, glycerol di(meth)acrylate, trimethylolpropane tri(meth)acrylate, pentaerythritol tetra(meth)acrylate, allyl methacrylate, allyl acrylate.

The terms 'soluble', 'mostly soluble', 'not fully soluble', and 'not soluble' are used to describe the extent which a composition which is capable of being dissolved in a reference liquid of interest.

The term 'soluble' is used to describe the composition of interest which dissolves completely in the reference liquid of interest. The term 'mostly soluble' is used to describe a composition which is capable dissolves completely with exception of a slight cloudiness in the reference liquid of interest. The term 'not fully soluble' is used to describe a composition which disperses with a cloudiness in the reference liquid of interest. The term 'not soluble' is used to describe a composition which does not disperse and remains as a solid in the reference liquid of interest. A list of solvents and non-solvent for polymers can be found in "Polymer Handbook, 4$^{th}$ Ed." edited by Brandrup J.; Immergut, Edmund H.; Grulke, Eric A.; Abe, Akihiro; Bloch, Daniel R., John Wiley & Sons: 2005. One skilled in the art is able to make a visual determination of the solubility or lack of solubility of the monomers chosen to confer this property on the star macromolecules.

Multi-arm stars macromolecules are the preferred topology for the present invention as they can adopt a globular shape wherein the inner segment, $(M2)_{p2}$ of each arm covalently attached to the core, can chain extend in a selected solvent to attain a highly swollen stable structure. The dispersant medium can be water, oil or mixture thereof. The degree of polymerization p2 of the segment (M2), should be higher than that of p1 of segment (M1) to attain a highly swollen stable structure. A star macromolecule with p2>(3×p1) is more preferred.

In one embodiment of the invention in a star macromolecule described with formula (2) and shown in FIG. 1B, comprising a fraction of segmented (co)polymer arms [F-$(M1)_{p1}$-$(M2)_{p2}$], the average number of arms, n, should be greater than two per star, preferentially greater than three, and can comprise a mole fraction between 0.5 and 100% of the arms in the average star macromolecule. The ratio of n tom is more preferably between 100 and 0.1.

In one embodiment of the invention in a star macromolecule described with formula (3) and shown in FIG. 1C comprising a fraction of arms [F-$(M1)_{p1}$] the average number of arms, o, should be greater than two per star, preferentially greater than three, and can comprise a mole fraction between 0.5 and 100% of the arms in the average star macromolecule. The ratio of o to m is more preferably between 100 and 0.1.

The present invention can be exemplified by a multi-arm star macromolecule wherein the average number of arms in the star macromolecule is between 5 and 500, preferentially between 10 and 250.

In one embodiment of the invention the star macromolecule has a core which contains additional functionality and/or expanded free volume. 'Expended free volume' of the core is defined as the core with lower crosslink density. The free volume in the core is generated when during the crosslinking process crosslinker Mx with monomer M2 or My is used. If M2 or My are monomers with functional groups, these groups will be incorporated in the core.

In one embodiment of the invention the star macromolecule may store and release in controlled rate the small molecules. 'Small molecules' are fragrances, UV absorbers, vitamins, minerals, dyes, pigments, solvents, surfactants, metal ions, salts, oils, or drugs. These small molecules can be stored inside the core of the star macromolecule and next released. Each small molecule has some affinity to the core, is soluble in the core environment. Higher affinity of the small molecule to the core will result in the lower rate of release from star macromolecule. The affinity may be increased or decreased through non-covalent forces including H-bonding, electrostatic, hydrophobic, coordination and metal chelating interactions.

In one embodiment of the invention the star macromolecule displays shear thinning behavior. 'Shear thinning' is defined as is an effect where viscosity decreases with increasing rate of shear stress. The extent of shear thinning behavior is characterized using a Brookfield-type viscometer where viscosities are measured under different shear rates.

In one embodiment of the invention the star macromolecule comprises a functional group which exhibits H-bonding, coordination, hydrophobic, metal chelating and/or electrostatic forces. "F" represents an optionally functional group or mixture of functional groups present on the arm chain-end. Functional groups (F) encompass all of the compounds capable of interacting through non-covalent forces including H-bonding, electrostatic, hydrophobic, coordination and metal chelating.

Some examples of F end groups capable of H-bonding include but are not limited to modified bases adenine, thymine, guanine, cytosine, or derivatives thereof, peptides etc. Some examples of endgroups capable of electrostatic interactions include but are not limited to carboxylate, phosphate, sulfonate, secondary-, tertiary- and quaternary-amines. Some examples of endgroups capable of hydrophobic interactions include but are not limited to C1-C30 aliphatic groups, benzyl and aliphatic benzyl groups, saturated and unsaturated hydrophobes. Some examples of endgroups capable of coordination interactions include but are not limited to metal ions and/or metal ion ligands. Some examples of endgroups capable of metal chelating interactions include derivatives of diethylenetriamine-N,N,N',N', N"-pentaacetic acid (DTA), ethylenedinitrilotetraacetic acid (EDTA), or nitrilotriacetic acid (NTA).

In one embodiment of the invention the star macromolecule comprises a functional group F which is designed to interact with small molecule surfactant micelles, 'Interacts with' is defined as any intermolecular force between two molecules. These intermolecular forces include electrostatic, hydrogen bonding, hydrophobic, steric, dipole-dipole, pi-pi, or other intermolecular forces.

Surfactants represent a class of molecules with a hydrophobic tail and a hydrophilic head. Some examples of surfactants include but are not limited to linear alkylbenzenesulfonate salts (LAS), alkyl ether sulfate salts (AEOS), alkylpolyglycosides (APG), alcohol ethoxylates, fatty acid glucoamides, betaines, alpha-olefinsulfonate salts, polysorbates, PEGs, alkylphenol ethoxylates, esterquats, imidizolium salts, diamido quaternary ammonium salts, etc.

In one embodiment of the invention the star macromolecule arms comprise a (co)polymer segment that exhibits an upper, or higher, critical solution temperature (UCST or HCST) whereby the star macromolecule is soluble in a liquid at higher temperature, say above 44° C., then at the lower use temperature the outer shell polymer segments become insoluble and self assemble to form a shear sensitive gel or in another embodiment the invention the outer shell of the star macromolecule arms comprise a (co)polymer segment that exhibits a lower critical solution temperature (LCST), say 5° C., whereby the star macromolecule is soluble in a liquid at lower temperature then at the use temperature the outer shell polymer segments become insoluble and self assemble to form a shear sensitive gel. In the case of a LCST it is envisioned that a copolymer segment with an LCST below 10° C., preferable below 5° C. would be optimal. A non-limiting example would be a copolymerization of BuMA and DMAEMA and preparation of copolymers with designed LCST. A copolymer with 10% BuMA has a LCST close to 0° C. and one would use less BuMA or a less hydrophobic monomer such as MMA to increase the LCST to ~5° C. Indeed the Tg of the segment of the star can be selected to allow dissolution of the star in room temperature aqueous media.

In one embodiment of the invention a star macromolecule further comprise a personal care and cosmetics formulation and/or product. Personal care and cosmetic products include but are not limited to a shampoo, conditioner, hair lotion, tonic, hair spray, hair mousse, hair gel, hair dyes, moisturizer, suntan lotion, color cosmetic, body lotion, hand cream, baby skin-care product, facial cream, lipstick, mascara, blush, eyeliner, baby shampoo, baby moisturizer, baby lotion, shower gel, soap, shaving product, deodorant, bath cream, body wash, serum, cream, solid, gel, lubricant, jelly, balm, tooth paste, whitening gel, disposable towel, disposable wipe or ointment.

In one embodiment of the invention a star macromolecule further comprise a home care formulation and/or product. Home care products include but are not limited to a surface cleaner, window cleaner, laundry detergent, toilet cleaner, fabric cleaner, fabric softener, dish detergent, cleaning stick, stain stick, spray cleaners, sprayable formulations, lubricant, disposable towel or disposable wipe.

The polymer chains that comprise the arms are preferably provided with a molecular mass of greater than or equal to 500 which can range up to 2,000,000. This numbers correspond to p1, p2, p3 in the range of 5 up to 20,000 preferably in the range of 8 to 2,000.

In one example, the star macromolecules comprising segmented copolymers arms are directed at use in aqueous media. The stars comprise a crosslinked core, and arms comprising of water soluble copolymer $(M2)_{p2}$ and a hydrophobic (co)polymer Therefore in a in a non-limiting example the stars comprise a crosslinked core, and arms comprising an water soluble (co)polymer (e.g. poly(acrylic acid), poly(2-hydroxyethyl acrylate), poly(N-isopropylacrylamide), poly(ethylene glycol) methacrylate, quaternized poly(dimethylaminoethyl methacrylate), etc.) and a hydrophobic (co)polymer (e.g. polystyrene or substituted polystyrenes, poly(alkyl(meth)acrylate), etc.) or a hydrocarbon based segment. Suitable hydrocarbon based segments can comprise low molecular weight α-olefin. Lower molecular weight α-olefins are commercially available and higher molecular weight species can be prepared by telomerization of ethylene or ethylene propylene mixtures. [Kaneyoshi, H.; Inoue, Y.; Matyjaszewski, K. *Macromolecules* 2005, 38, 5425-5435.]

The polymer compositions of the invention can self assemble in solution to provide a certain level of control over viscosity and consistency factors in many aqueous and oil based systems where control over the rheology is a concern. Applications include; water- and solvent-based coating compositions, paints, inks, antifoaming agents, antifreeze substances, corrosion inhibitors, detergents, oil-well drilling-fluid rheology modifiers, additives to improve water flooding during enhanced oil recovery, dental impression materials, cosmetic and personal care applications including hair styling, hair conditioners, shampoos, bath preparations, cosmetic creams, gels, lotions, ointments, deodorants, powders, skin cleansers, skin conditioners, skin emollients, skin moisturizers, skin wipes, sunscreens, shaving preparations, and fabric softeners, with the rheology modifier providing characteristics of high gel strength, highly shear thinning characteristics, forms versatile low viscosity soluble concentrations, and synergistic interactions with added agents to adjust their rheology profile to optimize properties such as sedimentation, flow and leveling, sagging, spattering, etc.

One non-limiting field of applications that can exemplify the utility of the disclosed star macromolecules is cosmetic and personal care compositions such as hair styling sprays, mousses, gels and shampoos, frequently contain resins, gums and adhesive polymers to provide a variety of benefits, for example, film-forming ability, thickening, sensory properties and hair shaping and setting. Polymers designed for rheological control, as thickening agents, in such compositions generally focus on linear or graft copolymers which contain various monomers in an alternating, random or block configuration.

Synthesis of the Rheology Modifier

Although any conventional method can be used for the synthesis of the multi-arm star macromolecules of the invention, free radical polymerization is the preferred and living/controlled radical polymerization (CRP) is the most preferred process.

CRP has emerged during the past decade as one of the most robust and powerful techniques for polymer synthesis, as it combines some of the desirable attributes of conventional free radical polymerization (e.g., the ability to polymerize a wide range of monomers, tolerance of various functionality in monomer and solvent, compatibility with simple industrially viable reaction conditions) with the advantages of living ionic polymerization techniques (e.g., preparation of low polydispersity index ($PDI=M_w/M_n$) polymer and chain-end functionalized homo- and block (co)polymers). The basic concept behind the various CRP procedures is the reversible activation of a dormant species to form the propagating radical. A dynamic and rapid equilibrium between the dormant and the active species minimizes the probability of bimolecular radical termination reactions and provides an equal opportunity for propagation to all polymer (or dormant) chains.

CRP procedures can be classified into three main groups based on the mechanism of reversible activation: (a) stable free radical polymerization (SFRP, Scheme 1a), (b) degenerative chain transfer polymerization (DT, Scheme 1b), and (c) atom transfer radical polymerization (ATRP, Scheme 1c).

Scheme 1. Three main groups of controlled radical polymerization based on the mechanism of reversible activation: (a) stable free radical polymerization (SFRP), (b) degenerative chain transfer polymerization (DT), and (c) atom transfer radical polymerization (ATRP).

(a) Stable free radical polymerization (SFRP)

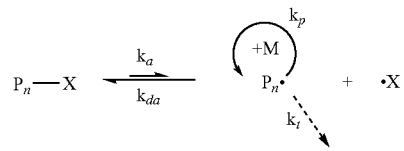

(b) Degenerative chain transfer polymerization (DT)

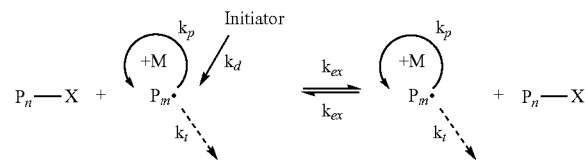

(c) Atom transfer radical polymerization (ATRP)

-continued $P_n$—X +

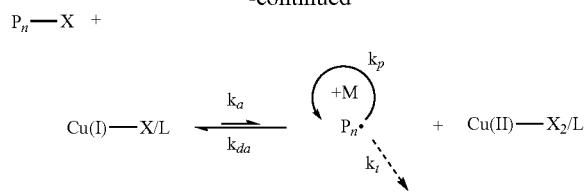

As shown in Scheme 1 various capping agents, X, are used for the different CRP procedures and they are summarized in Scheme 2. They include stable nitroxides (Scheme 2a), transition metal complexes (Scheme 2b), halides with transition metal catalysts (Scheme 2c), iodine with catalysts (Scheme 2d), sulfur compounds (Scheme 2e), iodine (Scheme 2f), and organometal compounds (Scheme 2g).

Scheme 2. Examples of capping agent X.

(a) Nitroxides (NMP)

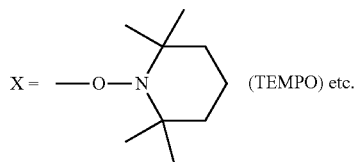 (TEMPO) etc.

(b) Transition metal complexes

X = 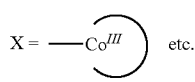 etc.

(c) Halides with transition metals (ATRP)

X = 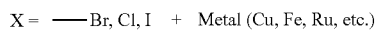  —Br, Cl, I  +  Metal (Cu, Fe, Ru, etc.)

(d) Iodide with catalysts (RCTP)

X = —I  +  Ge, Sn, etc.

(e) Dithioester, dithiocarbamate, and xanthate (RAFT)

X = 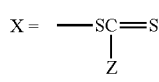

(Z = Ph, CH$_3$,
NEt$_2$, OEt, etc.)

(f) Iodine (ITP)

X =  —I (g) Tellurium, stibine, and bismuth compounds (TERP, SBRP, and BIRP)

X =  —RR'

(R = Te,
Sb, or BI,
R' = CH$_3$, etc.)

Star polymers are nano-scale materials with a globular shape. As illustrated in FIG. 1, stars formed by the "arm first" procedure, discussed in detail below, can have a crosslinked core and can optionally possess multiple segmented arms of similar composition. Stars can be designed as homo-arm stars or mikto-arm stars. FIG. 1A represents a homo-arm star with block copolymer arms. Mikto-arm stars have arms with different composition or different molecular weight; FIGS. 1 B and 1 C. Both homo-arm stars and mikto-arm stars can optionally possess a high-density of peripheral functionality.

Synthesis of star polymers of the invention can be accomplished by "living" polymerization techniques via one of three strategies: 1) core-first" which is accomplished by growing arms from a multifunctional initiator; 2) "coupling-onto" involving attaching preformed arms onto a multifunctional core and the 3) arm-first" method which involves cross-linking preformed linear arm precursors using a divinyl compound While all above controlled polymerization procedures are suitable for preparation of the disclosed self assembling star macromolecules the present disclosure will exemplify the preparation of the self assembling multi-arm stars with narrow MWD, in contrast to prior art using ATRP. The reason for the use of the Controlled Radical Polymerization process (CRP) known as ATRP; disclosed in U.S. Pat. Nos. 5,763,546; 5,807,937; 5,789,487; 5,945,491; 6,111,022; 6,121,371; 6,124,411; 6,162,882; and U.S. patent application Ser. Nos. 09/034,187; 09/018,554; 09/359,359; 09/359,591; 09/369,157; 09/126,768 and 09/534,827, and discussed in numerous publications listed elsewhere with Matyjaszewski as co-author, which are hereby incorporated into this application, is that convenient procedures were described for the preparation of polymers displaying control over the polymer molecular weight, molecular weight distribution, composition, architecture, functionality and the preparation of molecular composites and tethered polymeric structures comprising radically (co)polymerizable monomers, and the preparation of controllable macromolecular structures under mild reaction conditions.

The present invention relates to the preparation and use of multi-arm star macromolecules by an "arm first" approach, discussed by Gao, H.; Matyjaszewski, K. *JACS*: 2007, 129, 11828. The paper and cited references therein are hereby incorporated by reference to describe the fundamentals of the synthetic procedure. The supplemental information available within the cited reference provides a procedure for calculation of the number of arms in the formed star macromolecule.

It is expected that biphasic systems such as a miniemulsion or an ab initio emulsion system would also be suitable for this procedure since miniemulsion systems have been shown to function as dispersed bulk reactors [Min, K.; Gao, H.; Matyjaszewski, K. *Journal of the American Chemical Society* 2005, 127, 3825-3830] with the added advantage of minimizing core-core coupling reactions based on compartmentalization considerations.

In one embodiment star macromolecules are prepared with composition and molecular weight of each segment predetermined to perform as rheology modifiers in aqueous based solutions. The first formed segmented linear (co) polymer chains are chain extended with a crosslinker forming a crosslinked core.

In another embodiment a simple industrially scalable process for the preparation of star macromolecules is provided wherein the arms comprise segments selected to induce self assembly and wherein the self assemblable star macromolecules are suitable for use as rheology control agents in waterborne and solvent-borne coatings, adhesives, cosmetics and personal care compositions.

The invention is not limited to the specific compositions, components or process steps disclosed herein as such may vary.

It is also to be understood that the terminology used herein is only for the purpose of describing the particular embodiments and is not intended to be limiting.

The procedure for the preparation of star macromolecules may be exemplified by (co)polymerization of linear macromolecules, including macroinitiators (MI) and macromonomers (MMs), with a multi-vinyl cross-linker, a divinyl crosslinker is employed in the exemplary examples disclosed herein, to form a core of the star. The formation of the core of the star can also be formed through a copolymerization reaction wherein a monovinyl monomer is added to expand the free volume of the core to allow incorporation of additional arms into the congested core forming environment or to provide sufficient free volume within the core of the star to encapsulate functional small molecules. A molecule that functions as an initiator and a monomer, an inimer, can also be employed in the preparation of the core of the star macromolecule. When added to the reaction it functions to form a three arm branch in the core of the molecule and hence acts in a manner similar to the added monomer to increase the free volume within the star core.

The volume fraction of the core of the star can be controlled by appropriate selection of the crosslinker molecule or by conducting a copolymerization between the crosslinker and a vinyl monomer or an inimer. The composition of the core can be selected to provide an environment to encapsulate small molecules, such as fragrances, and control the rate of diffusion of the fragrance from the self assembled thickening agent after deposition on a part of the human body.

The core of the star polymers may contain additional functionality. This additional functionality can be of direct utility in certain applications or can be employed to tether or encapsulate further functional materials such as fragrances, stimuli responsive molecules or bio-responsive molecules to the core of the star by chemical or physical interactions.

The star macromolecules can be prepared in dilute solution when reaction conditions and crosslinker are chosen to avoid or reduce star-star coupling reactions.

The synthesis of multi-arm star polymers where the periphery of the star polymers contains additional functionality is possible. This functionality can be introduced by use of an initiator comprising the desired α-functionality in the residue of the low molecular weight initiator remaining at the α-chain end of each arm.

The present invention can be exemplified by the preparation of a multi-arm star macromolecule wherein the number of arms in the star macromolecule is between 5 and 500, preferentially between 10 and 250, with segments selected to induce self assembly when the star macromolecule is dispersed in a liquid wherein the self assemblable star macromolecules are suitable for use as thickening agents or rheology modifiers in cosmetic and personal care compositions at low concentrations of the solid in the thickened solution, preferably less than 5 wt %, and optimally less than 1 wt %. The dispersion medium can comprise aqueous based systems or oil based systems.

The structure of an exemplary new thickening agent, or rheology modifier, is a multiarm segmented star macromolecule wherein the core is prepared by controlled radical polymerization using an arm-first method. Scheme 3 provides a simple four step procedure that can be employed for preparation of an initial non-limiting exemplifying case the procedure is an atom transfer radical polymerization arm first macroinitiator method. In this approach the precursor of the arm(s) comprise a linear copolymer chain with a single terminal activatable group, as will be understood by one skilled in the art, having this disclosure as a guide, the activatable arm precursor will have a co-terminal functionality that under the conditions of the polymerization procedure can reversibly generate a radical. Scheme 3 illustrates the concept by sequential polymerization of styrene and tBA. These monomers are purely exemplary monomers and should not limit the applicability of the procedure in any manner since other monomers of similar phylicity can be employed. In Scheme 3 the polystyrene segment can be considered the outer shell of the star and the final poly (acrylic acid) segments the inner water soluble shell and the segment formed by chain extending the linear copolymer macroinitiators by reaction with the divinylbenzene crosslinker the core of the star.

Scheme 3. Multistep synthesis of PSt-b-PAA block copolymer stars

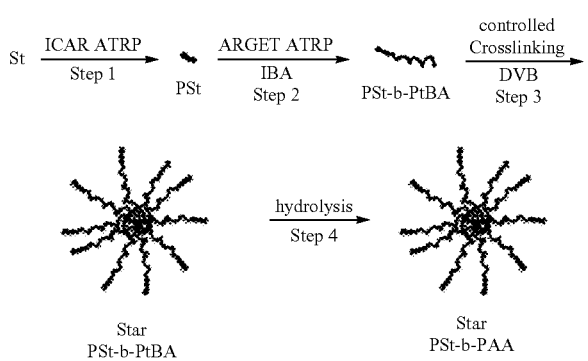

Similar structures can also be prepared using the macromonomer method or a combination of the macromonomer and macroinitiator method in a controlled polymerization process, or even through free radical copolymerization conducted on macromonomers, as known to those skilled in the art. [Gao, H.; Matyjaszewski, K. Chem—Eur. J. 2009, 15, 6107-6111.]

Both the macromonomer and macroinitiator procedures allow incorporation of polymer segments prepared by procedures other than CRP [WO 98/01480] into the final star macromolecule. Polymer segments can comprise segments that are bio-degradable of are formed from monomers prepared from biological sources.

As noted above the first formed ATRP macroinitiator can be prepared by conducting a sequential ATRP (co)polymerization of hydrophobic and hydrophilic monomers or precursors thereof or can be prepared by other polymerization procedures that provide a functional terminal atom or group that can be converted into an ATRP initiator with a bifunctional molecule wherein one functionality comprises a transferable atom or group and the other functionality an atom or group that can react with the functionality first present on the (co)polymer prepared by a non-ATRP procedure. [WO 98/01480]

In aqueous solutions, the composition and molecular weight of the outer shell of hydrophobes, or agents that participate in molecular recognition, can be selected to induce self-assembly into aggregates and act as physical crosslinkers. Above a certain concentration, corresponding to the formation of a reversible three dimensional network, the solutions will behave as physical gels thereby modifying the rheology of the solution.

The polymer compositions of the invention have significantly lower critical concentration for network (gel) formation compared to networks formed with block copolymers, graft and stars with a low specific number of attached arms due to:
multi-arm structure (many transient junctions possible between hydrophobic parts of the stars)
very high molecular weight of each star (5 thousand to 5 million or higher) allows high swelling ratio of the molecules in solution molecular organization on larger scales (>1 µm)

Whereas the examples above and below describe the preparation and use of block copolymers as arms with a well defined transition from one segment to the adjoining segment a segmented copolymer with a gradient in composition can also be utilized. The presence of a gradient can be created by addition of a second monomer prior to consumption of the first monomer and will affect the volume fraction of monomer units present in the transition form one domain to another. This would affect the shear responsiveness of the formed star macromolecule.

Star macromolecules with narrow polydispersity comprising arms with block copolymer segments can be formed with as few as 3 arms by selecting appropriate concentration of reagents, crosslinker and reaction temperature.

Star macromolecules can be prepared in a miniemulsion or reverse miniemulsion polymerization system. The first formed block copolymers are used as reactive surfactants for star synthesis by reaction with a selected crosslinker in miniemulsion.

EXAMPLES

Abbreviations

St, styrene
tBA, tertiary-butyl acrylate
AA acrylic acid
HEA hydroxyethyl acrylate
DMAEMA 2-(dimethylamino)ethyl methacrylate
PEGMA (polyethylene glycol) methacrylate
NIPAM N-isopropylacrylamide
DEBMM, diethylbromomethymalonate
TPMA, tris(2-pyridylmethyl)amine
AIBN, azobisisobutyronitrile
$Sn(EH)_2$ tin(II) 2-ethylhexanoate
DVB divinylbenzene
TFA trifluroacetic acid
THF tetrahydrofuran
NaOH sodium hydroxide Synthesis, Purification and Properties of Star Thickening Agent.

The initial examples of a star thickening agents with the structure shown below in FIG. 1 as structure A, are star macromolecules with PSt-b-PAA arms or PSt-b-P(HEA) arms.

Example 1

Preparation of a $(PSt-b-PAA)_x$ Star Macromolecule

The simple four step procedure was developed for the preparation of a poly(acrylic acid) based star macromolecule is described in Scheme 3. 1 kg of the star macromolecule with PSt-b-PtBA arms was prepared as follows.

Step 1:

Synthesis of a polystyrene macroinitiator using ICAR ATRP. The reaction conditions are $St/DEBMM/CuBr_2/TPMA/AIBN=50/1/0.002/0.003/0.05$ in bulk at T=60° C., t=10.2 h. The reaction was run to ~30% conversion resulting in the molecular weight of the hydrophobic, polystyrene segment=1600 which is equivalent to an average degree of polymerization (DP) of 16.

Figure 2:
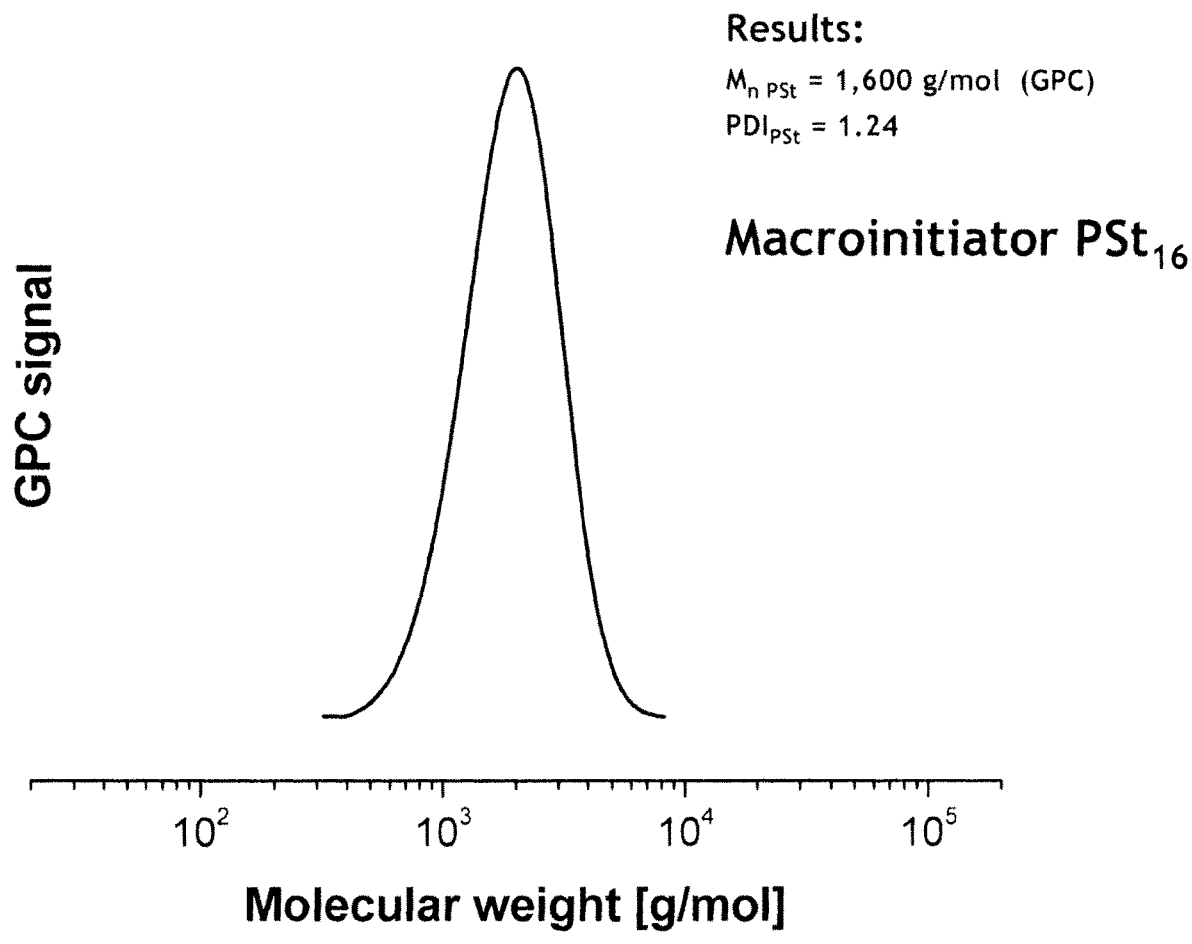
FIG. 2: GPC curve for the polystyrene macroinitiator formed in step 1 of the synthesis of an exemplary (PSt-b-PAA) star macromolecule.

The GPC trace obtained for the macroinitiator is shown in FIG. 2.

Figure 3:
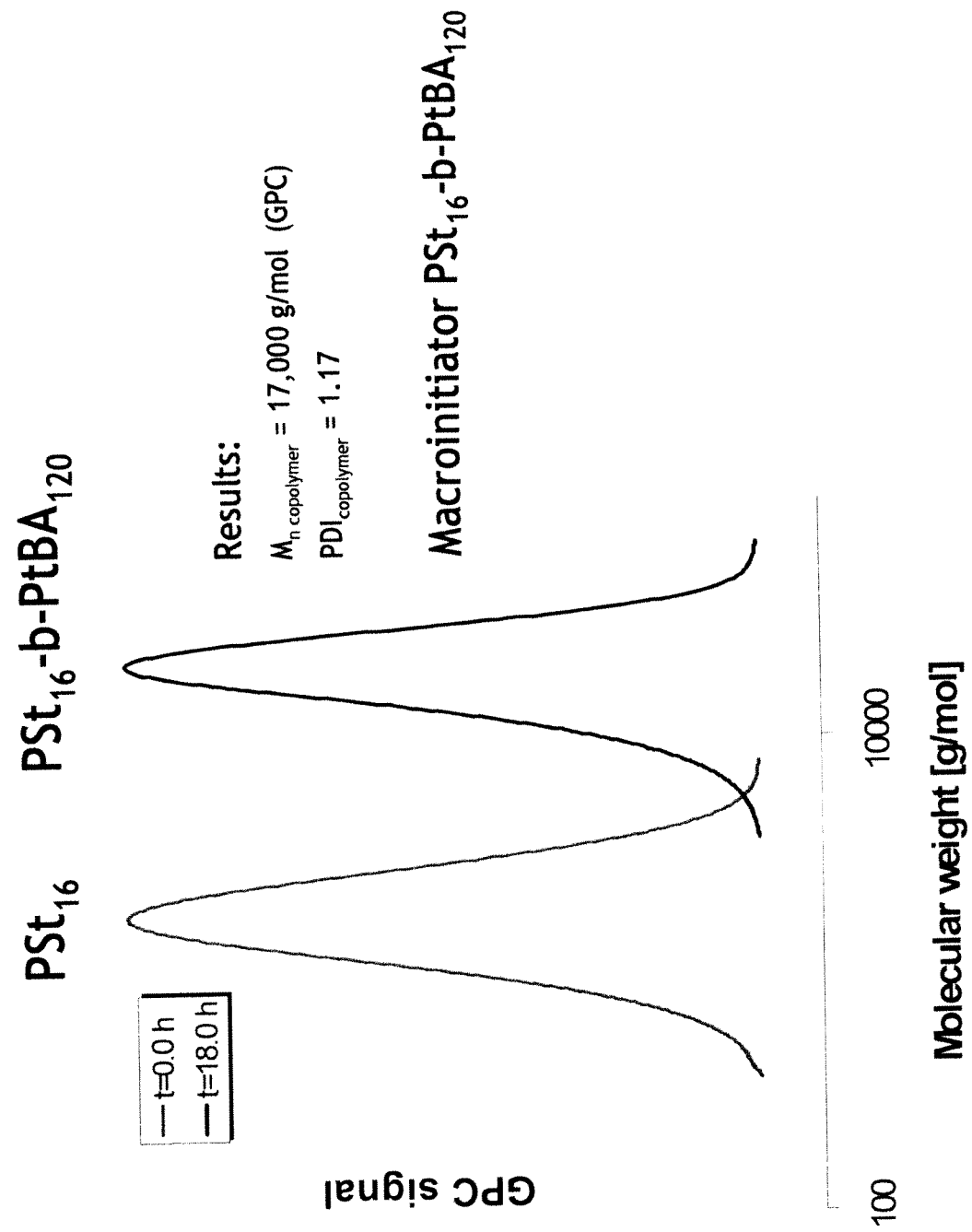
FIG. 3: GPC curves for the polystyrene macroinitiator formed in step 1 of the synthesis of an exemplary (PSt-b-PAA) star macromolecule and GPC curve for block copolymer formed after chain extension with tBA in step 2 of the synthesis.

Step 2:

Synthesis of polystyrene-b-poly(t-butyl acrylate) segmented block copolymer macroinitiator. The reaction conditions for the synthesis of PSt-b-PtBA macroinitiator arm are: $tBA/PSt/CuBr_2/TPMA/Sn(EH)_2=200/1/0.01/0.06/0.008$ in anisole (0.5 volume eq. vs. tBA), T=55° C., t=18.0 h. A higher molecular weight precursor of the water soluble segment was targeted to allow significant degree of swelling of the inner shell of the final functional star macromolecule. The final molecular weight of the poly(t-butyl acrylate) segment in the block copolymer was ~15,400 which is equivalent to a DP=120. The GPC curves of the polystyrene macroinitiator and the formed block copolymer macroinitiator is shown in FIG. 3 and clearly indicates that a clean chain extension had occurred.

Step 3:

Synthesis of the (PSt-b-PtBA)x Star Macromolecule.

A multi-arm star macromolecule was prepared by conducting a further chain extension reaction with the block copolymer macroinitiator formed in step 2. The reaction was conducted with a mole ratio of block copolymer to divinylbenzene of 1:12 in anisole.

Figure 4:
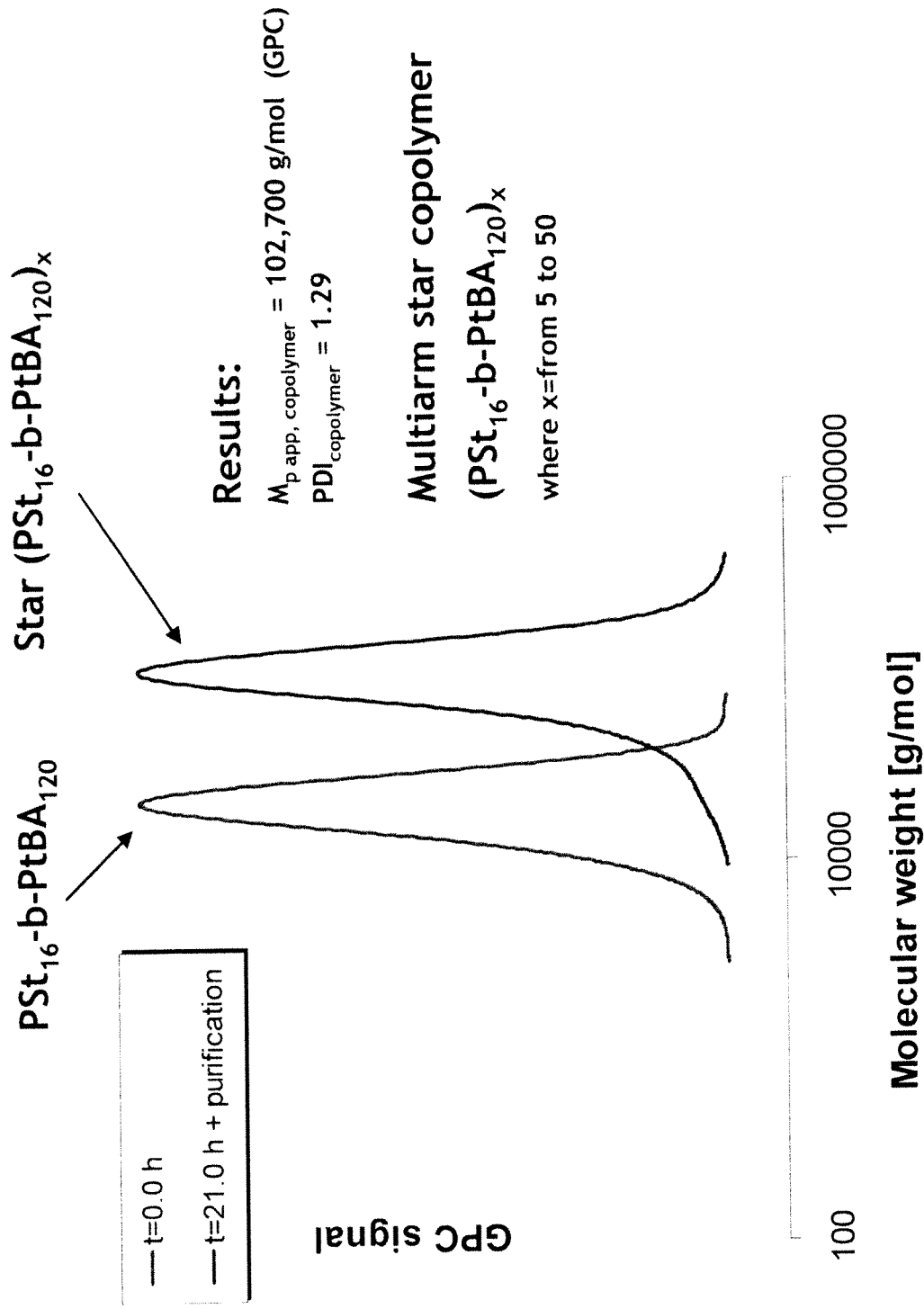
FIG. 4: GPC curves of the PSt-b-tBA block copolymer and the star macromolecule formed after core formation reaction is step 3 of the formation of an exemplary (PSt-b-PAA) star macromolecule.

The reaction conditions are: $DVB/PSt-b-PtBA/CuBr_2/TPMA/Sn(EH)_2=12/1/0.02/0.06/0.1$ in anisole (38 volume eq. vs. DVB), T=80° C., t=21.0 h). The GPC curves and results of the star forming reaction are provided in FIG. 4. It can be seen that a multi-arm star macromolecule with a crosslinked core was formed. The GPC molecular weight of the star was 102,700 with a PDI 1.29, which would indicate an average of six arms but this is an underestimate of the actual number of arms since the star molecule is a compact molecule. Indeed in this situation the number of arms in the star molecule is close to 30.

The number of arms can be modified by conducting the core forming reaction with a different ratio of crosslinking agent to arm precursor or by running the reaction with a different concentration of reagents.

Step 4:

Deprotection of the (PSt-b-PtBA)x star macromolecule to (PSt-b-PAA)x star block copolymer to provide water soluble poly(acrylic acid) segments in the multi-arm star macromolecule. The PSI-b-PtBA arms of the star macromolecule were transformed to PSt-b-PAA arms using a new procedure. Polymer was dissolved in methylene chloride and trifluoroacetic acid to deprotect tBu groups, the reaction was performed at room temperature for 60.0 h. Then polymer was decanted and washed 3 times with acetonitrile. Polymer was then solubilized in THF and precipitated into acetonitrile. The star macromolecule was dried in vacuum oven for 3 days at 50° C. The amount of polymer obtained after purification was 550 g, which would correspond to full conversion of PtBA to PAA.

Example 2

Properties of (PSt-b-PAA) Star Macromolecule as a Thickening Agent

Figure 5:
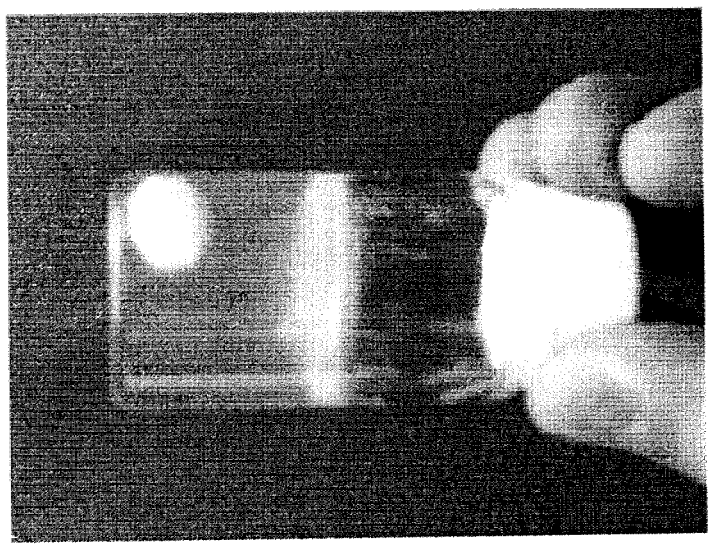
FIG. 5: Image showing the thickening properties of (PSt-b-PAA) star macromolecule.

The thickening properties of the final star macromolecule were investigated in aqueous solution. 100 mg of (PSt-b-PAA) star macromolecule was dissolved in 0.5 ml of THF and transferred to 10 ml of water. Solution was then neutralized with 2 ml of basic water (with NaOH). After few minutes of stirring gel was formed, see image in FIG. 5.

Figure 6:
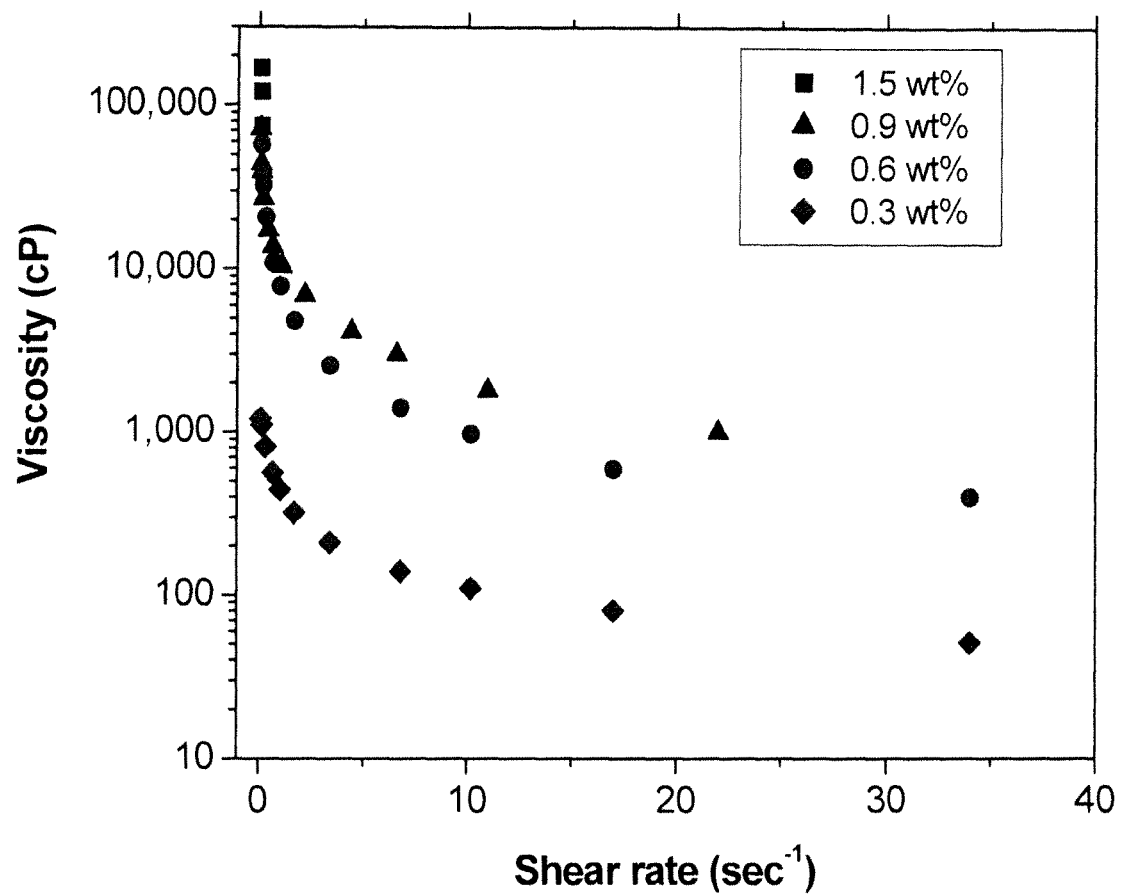
FIG. 6: Viscosity of aqueous solution of (PSt-b-PAA) star macromolecule vs. shear rate.

The rheological properties of the multi-arm star built with a longer poly(acrylic acid) (PAA) hydrophilic internal core segment and a short hydrophobic polystyrene (PSt) peripherial segment were then investigated. The viscosity of aqueous solutions containing different concentrations of the star macromolecule vs. shear rate were measured; using a Brookfield LVDV-E, Spindle #31 (or #34, #25) at a T=25° C., and the results are presented in FIG. 6. It is clear that even very low concentrations of the star macromolecule in water (<0.6 weight %) the apparent viscosity of the sample is very high (in the range of 50,000 to 100,000 centipoise (cP)).

In comparison, leading thickening agents on the market for personal care products (e.g. natural nonionic vegetable derived liquid thickener Crothix Liquid by CRODA or synthetic acrylate based copolymer DOW CORNING RM 2051) are used at the level of 2-5 weight % and only increase the viscosity of a water based solution up to 5,000-20,000 cP.

Figure 7:
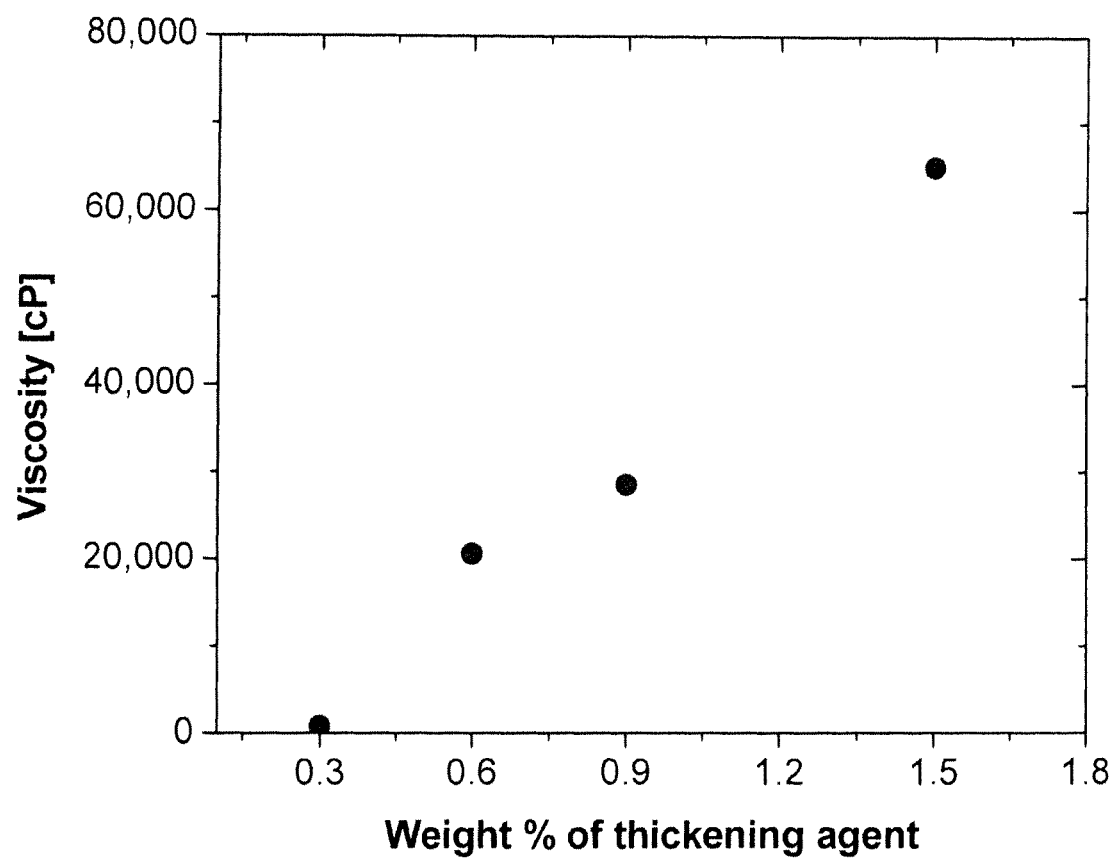
FIG. 7: Viscosity of aqueous solution of (PSt-b-PAA) star macromolecule vs. concentration.

FIG. 7 presences the viscosity of aqueous solution of a (PSt-b-PAA) star macromolecule vs. concentration. The measurement was conducted on a Brookfield LVDV-E with spindle #31 (or #34, #25) at a temperature=25° C. and rate=1 RPM. It can be seen that for this particular star macromolecule 0.3 weight % concentration of star macromolecule in water is a minimum amount for gel formation and that higher concentrations significantly increase the viscosity of the resulting solution.

Tests indicated that the thickening agent provided formulations that exhibited a lack of tackiness, a very pleasant feel on the skin.

Example 3

Figure 8:
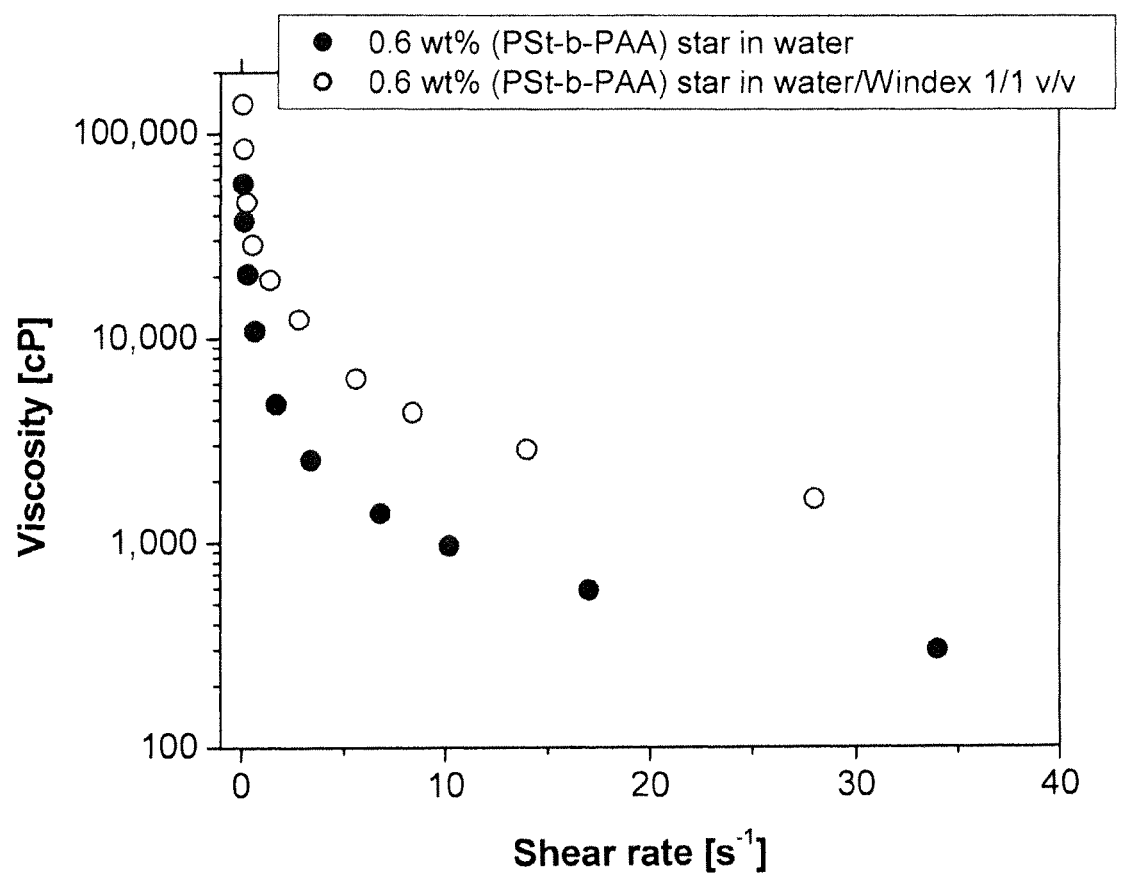
FIG. 8: Viscosity of an aqueous solution and a water/windex (1/1 v/v) solution of (PSt-b-PAA) star macromolecule vs. shear rate.
Figure 9:
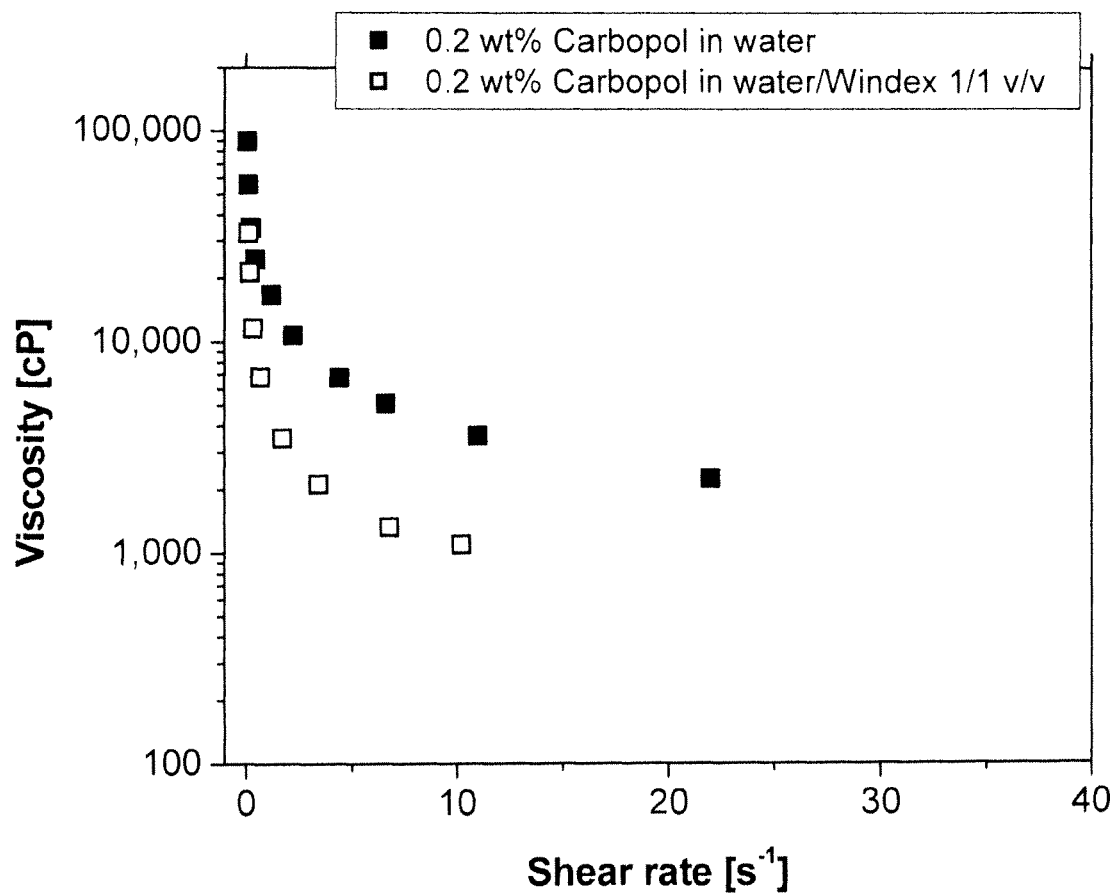
FIG. 9: Viscosity of an aqueous solution and a water/windex (1/1 v/v) solution of Carbopol EDT 2020 vs. shear rate.

Properties of (PSt-b-PAA) Star Macromolecule as Thickening Agents in Harsh Environments The thickening properties of the final star macromolecule were investigated in aqueous solution in the presence of an oxidizing agent and at high pH. FIG. 8 presents the viscosity of an aqueous solution of (PSt-b-PAA) star macromolecule and the viscosity of water/windex (1/1 v/v) solution of (PSt-b-PAA) star macromolecule and FIG. 9 presents the results obtained with Carbopol EDT 2020 in the same media. The pH of the aqueous solution was 6-7 while for the water/Windex solution pH=9-10. (Measurement of viscosity was conducted using a Brookfield LVDV-E, Spindle #31 (or #34, #25), T=25° C.) It can be seen that viscosity of water/windex solution is higher than that of water solution. The performance of (PSt-b-PAA) star macromolecule as thickening agent is not diminished in this harsh environment presented by the windex/water solution with a pH=9-10 resulting from the presence of high amount of ammonia-D. In comparison, the thickening properties of the leading thickener on the market, Carbopol EDT 2020, were decreased in similar conditions and FIG. 9 shows that the viscosity of water/windex solution is lower than that of pure aqueous solution.

It is envisioned that the poor performance of Carbopol vs. (PSt-b-PAA) star macromolecule as thickening agent in water/Windex solution is a consequence of the high amount of ester bonds in its structure which can interact with the ionic species present in such harsh environment or can be even degraded. On the other side (PSt-b-FAA) star macromolecule has only C—C bonds, which make this thickening agent stable in water/Windex solution and overall thickening performance is not decreased.

Example 4

Properties of (PSt-b-PAA) Star Macromolecule Vs. (PAA) Star Macromolecule as Thickening Agents A (PAA) star macromolecule was synthesized in order to compare its properties to those determined for the (PSt-b-PAA) star macromolecule. Synthesis of (PAA) star was performed in similar way as for synthesis of (PSt-b-PAA) star macromolecule but starting with pure PtBA arms.

Figure 10:
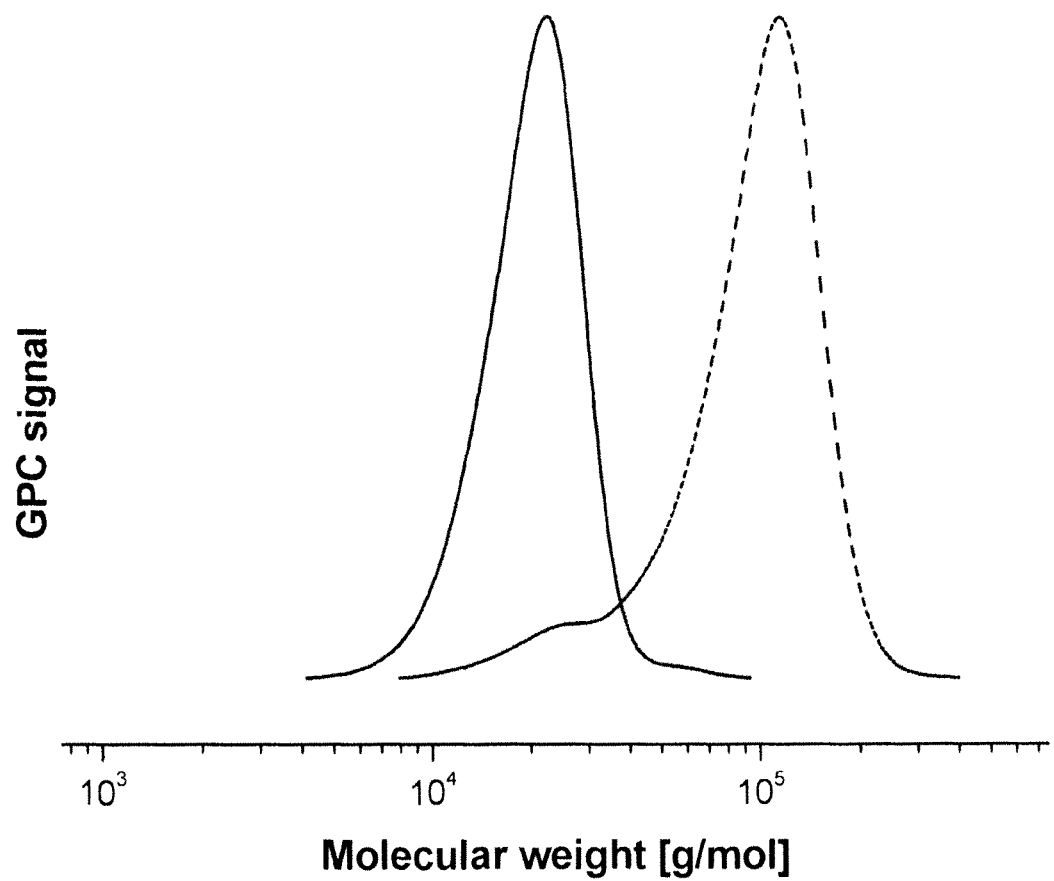
FIG. 10: GPC Curves for preparation of the precursor to a PAA star. Solid line PtBA $M_n$=18,900 PDI-1.14; Dashed line (PtBA)$_x$ star with $M_{n,app}$ 112,600 PDI=1.36
Figure 11:
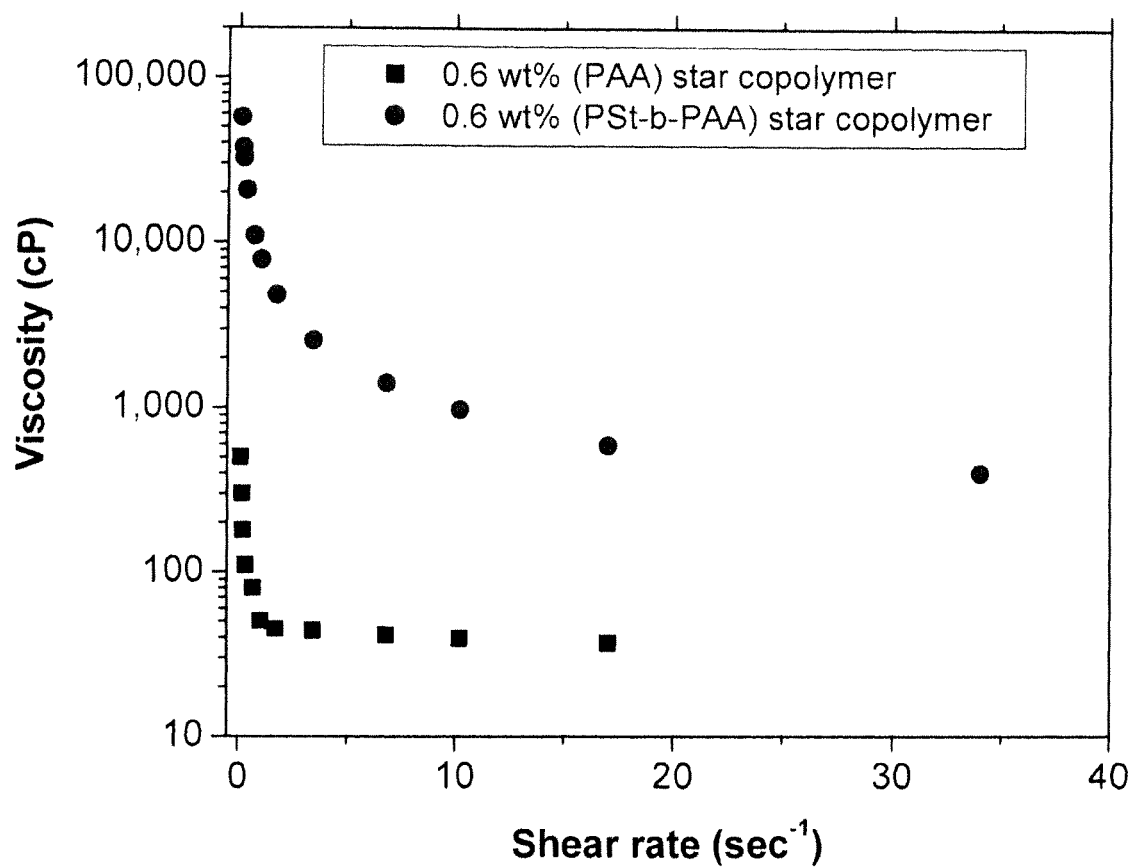
FIG. 11: Viscosity of aqueous solution of (PSt-b-PAA) star macromolecule and (PAA) star macromolecule vs. shear rate.

The final (PAA) star had similar molecular weight, number of arms and molecular weight distribution to the (PSt-b-PAA) star macromolecule, FIG. 10. The only one difference between two star macromolecules is the outer shell which comprises of PSt with degree of polymerization 16 in (PSt-b-PAA) star macromolecule whereas this star macromolecule posses pure PAA homo-polymeric arms. FIG. 11 presents the viscosity of aqueous solutions of (PSt-b-PAA) star and (PAA) star macromolecules. The measurement was conducted using a Brookfield LVDV-E fitted with a #31 spindle at a temperature=25° C. and pH=7. It can be seen that viscosity of star macromolecule with a hydrophobic outer shell has very strong thickening properties, where the pure (PAA) star has low thickening effect on water.

Therefore one can conclude that in order to thicken aqueous based media the proposed multi-arm star macromolecules have to have a blocky structure, with a hydrophilic inner shell and a hydrophobic outer shell. Without wishing to be limited by a proposed mechanism we believe these results in aqueous media can be explained by the induced self-assembly of the hydrophobic segments into aggregates, the hydrophobes act as "junctions" between aggregates, and above a certain concentration, a three-dimensional reversible physical network is formed with a behavior similar to conventional gels.

Example 5

(PSt-b-PAA) Star Macromolecule as Thickening and Emulsifying Agent

Figure 12:
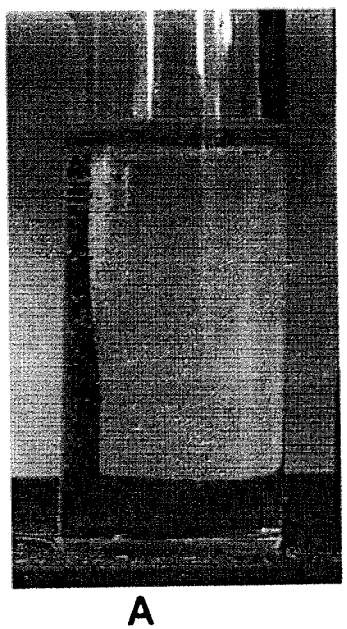
FIG. 12: Images demonstrating the emulsifying properties of (PSt-b-PAA) star macromolecule.
Figure 12:
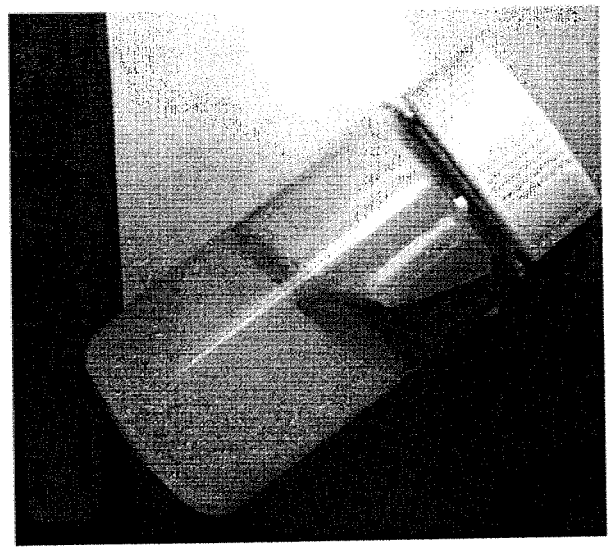

Due to its very well-defined structure, (PSt-b-PAA) multi-arm star macromolecule may act not only as a thickening agent but also as efficient emulsifying agent. FIG. 12 presents images demonstrating the emulsifying properties of (PSt-b-PAA) star macromolecule. First photograph shows mixture of water with 2 volume % of pure lemon oil. After vigorous mixing, water and oil quickly separated into two phases. The second photograph presents water with 2 volume % of lemon oil and 0.6 weight % of thickening agent. After vigorous mixing, the phase separation did not occur and thicken properties did not decrease. Solutions were shaken for 1 min and photographs were taken 2 h after mixing.

Its hydrophobic core (as well as hydrophobic outer shell) may act as a storage place for small organic molecules (e.g. vitamins, fragrances, sunblock agents, etc.). This provides for the possibility for delivery of functional organic molecules, e.g. fragrance for slow release or UV absorbing molecules in sunscreens to any part of the body in a pleasant feeling emulsion.

In order to provide an equivalent response for non-polar media the phylicity of the inner and outer shells would have to be reversed.

Example 6

Mikto-Arm Star Macromolecules

A multi-arm star macromolecule was synthesized. The procedures for forming the arms PSt-b-PtBA and PtBA were similar to that described in Example 1. Next, two different arms were crosslinked together to form a star macromolecule. Reaction conditions for core forming crosslinking reaction: DVB/[PSt-b-PtBA/PtBA]/CuBr2/TPMA/Sn(EH)2=17/1/0.02/0.06/0.2 in anisole (38 volume eq. vs. DVB), (1667 ppm of Cu) T=95° C., t=510 h, PSt-b-PtBA/PtBA=1/4. Next, PtBA was transformed to PAA by deprotection with acid as described in Step 4 in Example 1.

Figure 13:
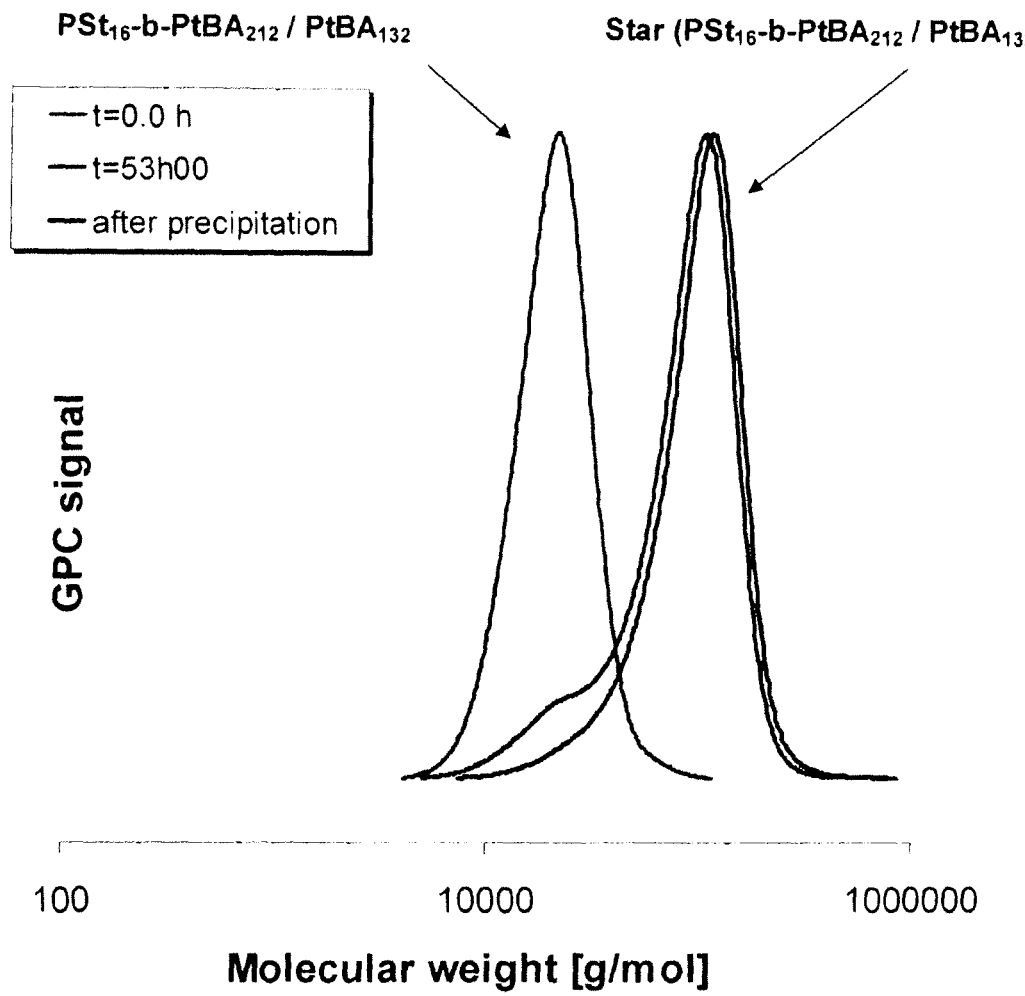
FIG. 13: Synthesis of [(PSt-b-PtBA)/(PtBA)] star macromolecule using arm-first method.
Figure 13:
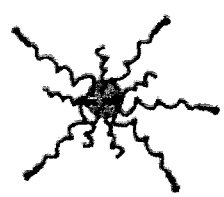
Figure 14:
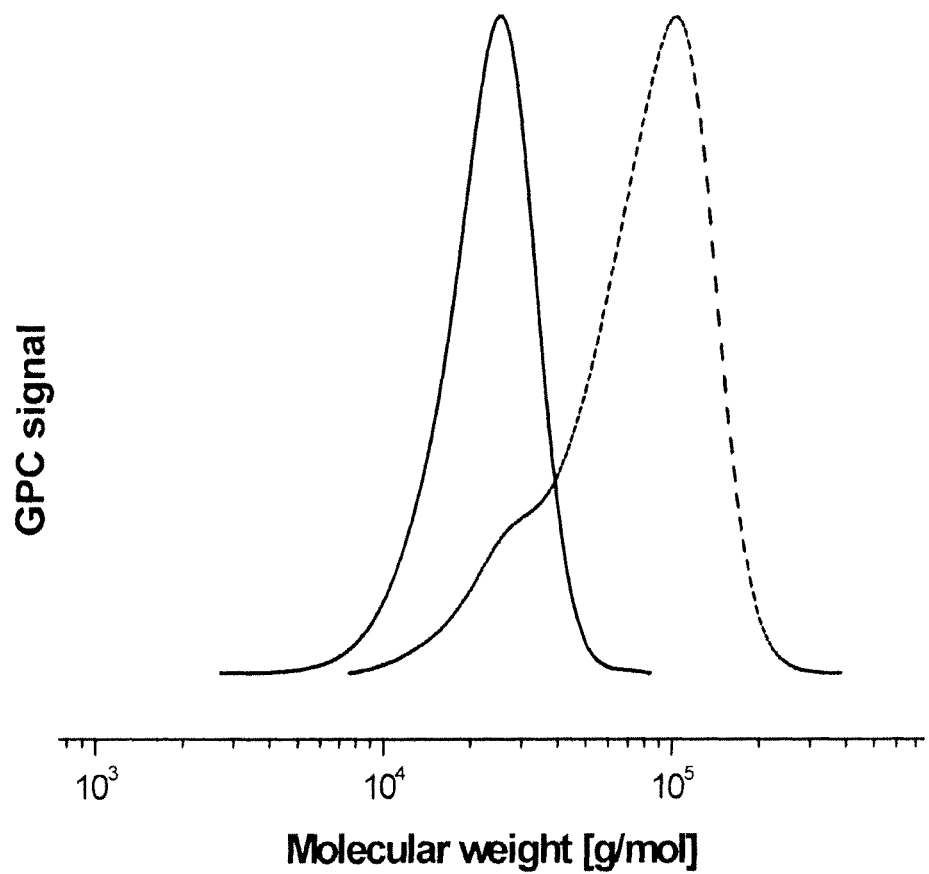
FIG. 14: GPC curves for $C_{18}$-PtBA arm star macromolecule, Solid line $C_{18}$-PtBA arm with $M_n$=19,200 PDI=1.16; dashed line ($C_{18}$-PtBA)$_x$ star macromolecule $M_{n,app}$=95,600 PDI=1.48.
Figure 15:
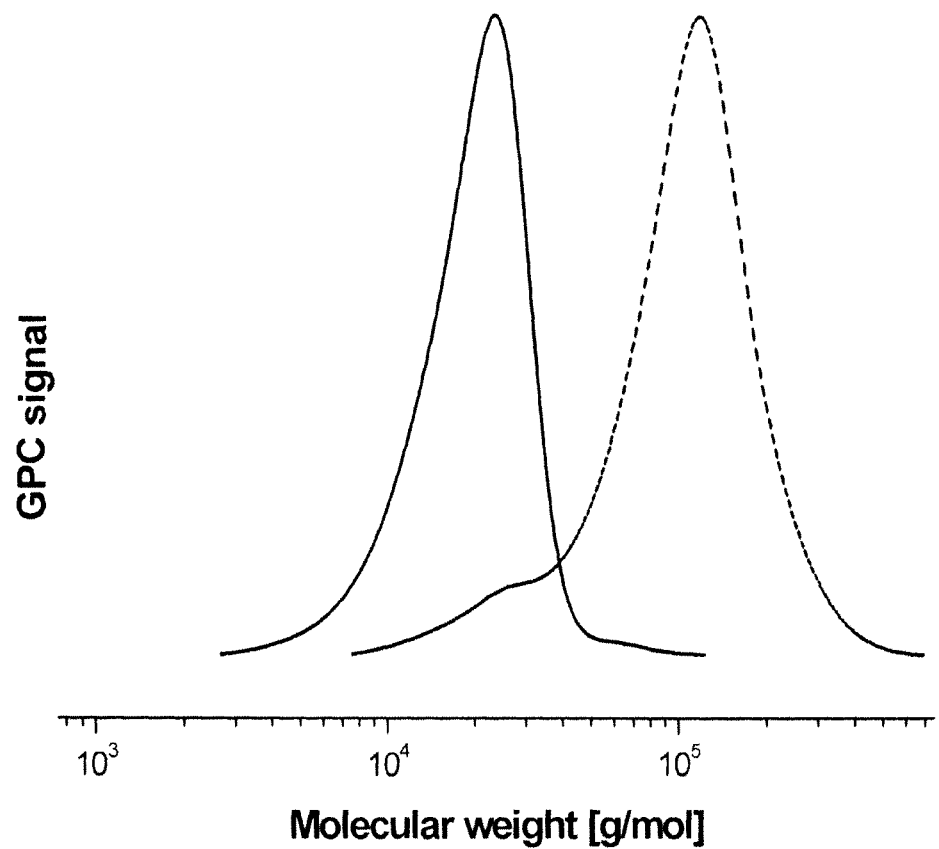
FIG. 15. GPC curves for $C_{12}$-PtBA arm star macromolecule, Solid Line $C_{12}$-PtBA $M_n$=17,500 PDI=1.22; Dashed line ($C_{12}$-PtBA)$_x$ $M_{n,app}$ 113,900 PDI=1.53.

FIG. 13 shows the GPC curves of the arms and the formed mikto-arm star macromolecule before and after purification by precipitation. Schematic 13B shows a representation of such a mikto-arm star macromolecule.

Synthesis of stars with lower amounts of the outer PSt block was successfully performed. Two stars were synthesized, one with 50% and one with 20% of PSt-b-PAA arms and 50% and 80% pure PAA arms (WJ-08-006-234 and WJ-06-235) by the procedures detailed above. Studies show that these star macromolecules can be dispersed directly in warm water. Thickening properties of these two new stars were as good as first exemplary star with 100% of PSt-b-PAA arms.

Stars with different outer hydrophobic shells can be prepared. One example that provides an outer shell which exhibits a Tg below use temperature is a star prepared with a PnBA outer shell.

Another approach which can reduce the cost of the preparing an outer hydrophobic shell is conversion of commercially available α-olefins to an ATRP initiator by reaction with a halo-alky(meth)acrylylhalide.

Example 7

Stars with Different Hydrophobic Segments

One parameter which may significantly change viscosity of thickening agent as well as its interaction with surfactant in shampoo formulations is the type of hydrophobic unit capped at the peripheral end of a fraction of the arms of the star macromolecule, Two additional stars were synthesized in order to compare to $(PSt_{16}\text{-}PAA_{120})_x$ (before deprotection: $M_{n,app}$=102,700 g/mol, PDI=1.29) star macromolecule. These stars include:

A) $C_{18}\text{-}PAA_{146})_x$: $M_{n,app}$=95,600 g/mol, PDI=1.48,
B) $C_{12}\text{-}PAA_{134})_x$: $M_{n,app}$=113,900 g/mol, PDI=1.53, Each star was prepared in three steps:
  i) preparation of PtBA arm,
  ii) crosslinking arms into star macromolecule,
  iii) deprotection of tBu groups. All of the stars had relatively low PDI with low amount of unreacted arms (<15 wt %).

A) A new PtBA macroinitiator was prepared from an initiator containing a linear $C_{18}$ alkyl chain for preparation of the $(C_{18}\text{-}PAA_{146})_x$ star. The synthesis of this arm precursor $C_{18}$-PtBA-Br was accomplished using ARGET ATRP of tBA using $C_{18}$ alkyl chain functionalized EBiB. The conditions and properties of synthesized polymer are shown in Table 1.

TABLE 1

Experimental conditions and properties of PtBA prepared by ARGET ATRP.[a]

| Entry | Molar ratios | | | | Cu [ppm] | Time (min) | Conv. (%) | $M_{n,\,theo}$[b] | $M_{n,\,GPC}$ | $M_w/M_n$ |
| --- | --- | --- | --- | --- | --- | --- | --- | --- | --- | --- |
| | tBA | I | CuBr$_2$ | L | RA | | | | | |
| 08-006-160 | 300 | 1 | 0.015 | 0.06 TPMA | 0.1 | 50 | 1380 | 47 | 18200 | 19700 | 1.19 |

[a] I = $C_{18}$-EBiB, L = Ligand, RA = reducing agent = Sn(EH)$_2$; [tBA]$_0$ = 4.67M; T = 60° C., in anisole (0.5 volume equivalent vs. monomer);
[b] $M_{n,\,theo}$ = ([M]$_0$/[$C_{18}$-EBiB]$_0$) × conversion This macroinitiator was than crosslinked using DVB into a star macromolecule. After deprotection of tBu groups by stirring the reaction for 3 days in the presence of TFA resulting in transformation to PAA units star was precipitated from $CH_2Cl_2$. The viscosity of resulting $(C_{18}\text{-}PAA)x$ star and the $(C_{12}\text{-}PAA)x$ star can be compared to (PSt-b-PAA)x in water and shampoo formulations.

Example 8

Stars with an Inner P(HEA) Shell

P(HEA) star macromolecules that comprise water soluble non-ionizable hydrophilic segments selected to make the star macromolecules compatible with solutions further comprising dissolved/dispersed salts that are additionally stable over a broad range of pH.

The PSt-b-PHEA arm precursor was prepared using ICAR ATRP. Conditions for the polymerizations and characterization of the resulting polymer are shown in Table 2. Polymerization was well controlled and well-defined block copolymer was prepared with relatively low (PDI=1.26 and 1.20). This is the first example of successful ICAR ATRP for acrylate type monomer. PSt-b-PHEA arm precursor was purified by precipitation into ethyl ether and dried under vacuum over two days at 50° C.

TABLE 2

Experimental conditions and properties of PSt-b-PHEA prepared by ICAR ATRP.[a]

| Entry | Molar ratios | | | | | Cu [ppm] | Time (min) | Conv. (%) | $M_{n, theo}$[b] | $M_{n, GPC}$ | $M_w/M_n$ |
| --- | --- | --- | --- | --- | --- | --- | --- | --- | --- | --- | --- |
| | HEA | I | $CuBr_2$ | L | RA | | | | | | |
| 08-006-155 | 200 | I | 0.04 | 0.04 TPMA | 0.1 | 200 | 1200 | 63 | 16100 | 30400 | 1.26 |
| 08-006-158 | 300 | I | 0.05 | 0.05 TPMA | 0.05 | 167 | 1230 | 54 | 20300 | 42300 | 1.20 |

[a]I = PSt (08-006-29, $M_n$ = 1600 g/mol, PDI = 1.20), L = Ligand, RA = reducing agent = AIBN; [HEA]$_0$ = 5.44M; T = 65° C., in DMF (0.7 volume equivalent vs. monomer);
[b]$M_{n, theo}$ = ([M]$_0$/[PSt]$_0$) × conversion.

Different crosslinking agents were investigated, including DVB and in run 08-006-159 di(ethylene glycol) diacrylate (DEGlyDA) and in run 08-006-161 DEGlyDA with small amount of HEA monomer. The reaction was not fully controlled when conversion of the added divinyl crosslinker was driven to high conversion as a consequence of star-star core coupling reactions resulted in gel formation. However at lower conversion of the crosslinker and under more dilute conditions star macromolecules were formed.

The disclosed star macromolecules can find utility in a spectrum of applications including, but not limited to; personal care: including shampoos/conditioners, lotions, serums, creams, solids, jelly, cosmetics: including mascara, blush, lip stick, powders, perfumes and home care: including cleaners for windows, household and work surfaces, toilet areas, laundry, and in dish and dishwasher applications.

What is claimed is:

1. A polymer composition comprising one or more star macromolecules formed by an arm-first living-controlled radical polymerization and having a core and a plurality of polymeric arms, wherein
   a) at least one arm of the plurality of polymeric arms is a polymeric arm; and
   b) at least one arm of the plurality of polymeric arms is a copolymeric arm, wherein:
      the copolymeric arm comprises a longer polymeric segment proximal to the core and a shorter polymeric segment distal to the core; and
   c) wherein at least one polymeric arm or copolymeric arm comprises one or more of a monomeric unit of an acrylamide, N,N-dimethylaminoethyl acrylate, N,N-dimethylaminoethyl methacrylate, N,N-dimethylaminoethyl acrylamide, quaternised N,N-dimethylaminoethyl acrylamide, N,N-dimethylaminoethyl methacrylamide, quaternised N,N-dimethyl aminoethyl methacrylamide, quaternised N,N-dimethyl-aminoethyl acrylate, quaternised N,N-dimethylaminoethyl methacrylate, and quaternized dimethylaminoethyl methacrylate; and
wherein the one or more star macromolecules are soluble in oil.

2. The polymer composition of claim 1, wherein the living-controlled radical polymerization is a RAFT, ATRP, NMP, TEMPO, RCTP, TERP, SBRP or BIRP polymerization.

3. The polymer composition of claim 1, wherein the living-controlled radical polymerization is a RAFT polymerization or ATRP polymerization.

4. The polymer composition of claim 1, wherein the star macromolecules are oil-soluble rheology-modifying star macromolecules.

5. The polymer composition of claim 1, wherein the one or more star macromolecules are thickeners for an oil-based system.

6. The polymer composition of claim 1, wherein the one or more star macromolecules provides rheology control over viscosity in an oil based system.

7. The polymer composition of claim 1, wherein the at least one copolymeric arm is a random, gradient, or block copolymeric arm.

8. The polymer composition of claim 1, wherein the plurality of polymeric arms, the at least one polymeric arm, or the at least one copolymeric arm, further comprises a monomeric unit of a styrene.

9. The polymer composition of claim 8, wherein the styrene is substituted with one or more C1-C12 straight or branched chain alkyl groups.

10. The polymer composition of claim 1, wherein the plurality of polymeric arms, the at least one polymeric arm, or the at least one copolymeric arm, further comprises a monomeric unit of: dodecyl acrylate, N-dodecyl methacrylamide, styrene, or 2-ethylhexyl methacrylate.

11. The polymer composition of claim 1, wherein the core comprises a polymerized monomeric residues of: 1,2-divinylbenzene; 1,3-divinylbenzene; 1,4-divinylbenzene; 1,2-ethanediol di(meth)acrylate; 1,3-propanediol di(meth)acrylate; 1,4-butanediol di(meth)acrylate; 1,5-hexanediol di(meth)acrylate; divinylbenzene; ethyleneglycol di(meth)acrylate; di(ethylene glycol) diacrylate (DEGlyDA); propyleneglycol di(meth)acrylate; butyleneglycol di(meth)acrylate; triethyleneglycol di(meth)acrylate; polyethyleneglycol di(meth)acrylate; polypropyleneglycol di(meth)acrylate; polybutyleneglycol di(meth)acrylate; allyl(meth)acrylate; glycerol di(meth)acrylate; trimethyloipropane tri(meth)acrylate; pentaerythritol tetra(meth)acrylate; allyl methacrylate; or allyl acrylate.

12. An oil based system additive, comprising the polymer composition of claim 1.

13. The polymer composition of claim 1, wherein the polymeric arm is shorter than the copolymeric arm.

* * * * *